US012757909B2

(12) United States Patent
Mimouni et al.

(10) Patent No.: US 12,757,909 B2
(45) Date of Patent: Oct. 13, 2026

(54) MICROPARTICULATION OF RECOMBINANT BETA-LACTOGLOBULIN AND ASSOCIATED FOOD APPLICATIONS

(71) Applicant: BON VIVANT, Lyons (FR)

(72) Inventors: Arnaud Mimouni, Lyons (FR); Kelly Mulder, Lyons (FR); Helene Briand, Lyons (FR); Lena Piola, Lyons (FR)

(73) Assignee: VERLEY, Lyons (FR)

(*) Notice: Subject to any disclaimer, the term of this patent is extended or adjusted under 35 U.S.C. 154(b) by 0 days.

(21) Appl. No.: 18/903,400

(22) Filed: Oct. 1, 2024

(65) Prior Publication Data

US 2025/0107546 A1 Apr. 3, 2025

(30) Foreign Application Priority Data

Oct. 2, 2023 (EP) .................................... 23306688

(51) Int. Cl.

| | |
|---|---|
| ***A23C 11/06*** | (2025.01) |
| ***A23J 1/00*** | (2006.01) |
| ***A23J 3/20*** | (2006.01) |
| ***A23P 30/00*** | (2016.01) |
| ***C07K 14/47*** | (2006.01) |

(52) U.S. Cl.

CPC ............. *A23C 11/065* (2013.01); *A23J 1/008* (2013.01); *A23J 3/20* (2013.01); *C07K 14/4717* (2013.01); *A23P 30/00* (2016.08)

(58) Field of Classification Search

CPC ........... A23C 11/065; A23J 3/20; A23J 1/008; C07K 14/4717; A23P 30/00

See application file for complete search history.

(56) References Cited

U.S. PATENT DOCUMENTS

| | | | | |
|---|---|---|---|---|
| 4,961,953 | A | 10/1990 | Singer et al. | |
| 5,795,611 | A | 8/1998 | Slattery | |
| 10,709,146 | B2 | 7/2020 | Mikkelsen et al. | |
| 10,729,150 | B2 | 8/2020 | Pedersen et al. | |
| 10,834,934 | B2 | 11/2020 | Mikkelsen et al. | |
| 2011/0262608 | A1 | 10/2011 | Burger | |
| 2016/0262424 | A1* | 9/2016 | Mikkelsen | A23C 21/06 |
| 2019/0216106 | A1 | 7/2019 | Geistlinger et al. | |
| 2022/0211061 | A1* | 7/2022 | Geistlinger | A61P 37/00 |

FOREIGN PATENT DOCUMENTS

| | | | | |
|---|---|---|---|---|
| CA | 3225417 | A1 | 12/2022 | |
| WO | 2006034857 | A2 | 4/2006 | |
| WO | 2015059248 | A1 | 4/2015 | |
| WO | 2016075332 | A1 | 5/2016 | |
| WO | 2018149869 | A1 | 8/2018 | |
| WO | 2020187842 | A1 | 9/2020 | |
| WO | WO2022239000 | A1 * | 11/2022 | C12N 1/16 |

OTHER PUBLICATIONS

Kew, B. et al., Review on fat replacement using protein-based microparticulated powders or microgels: A textural perspective, Trends in Food Science & Technology, 106 (2020) p. 457-468.
J. K. Keppler et al., Food Hydrocolloids 2023, 110, 106132, Towards recombinantly produced milk proteins: Physicochemical and emulsifying properties of engineered whey protein beta-lactoglobulin variants.
M. L. Diaz-Bustamante et al., Heliyon 2023, 9, e16974, "Trends and prospects in dairy protein replacement in yogurt and cheese".
Huppertz T., Burleigh Dodds Series in Agricultural Science, 2022, 114, "Understanding and improving the functional and nutritional properties of milk".
Ipsen, R., International Dairy Journal, 2016, "Microparticulated whey proteins for improving dairy product texture".
Kew B. et al.. Trends in Food Science & Technology 2020, 106, 457-468, "Review on fat replacement using protein-based microparticulated powders or microgels: A textural perspective".
Liou, B. K et al. Journal of Food Science, 2007, 72, S595-S604, "Effect of fat level on the perception of five flavor chemicals in ice cream with or without fat mimetics by using a descriptive test".
Liu, R. et al., Food Hydrocoll. 2018, 81, 39-47, "Fabricating Soy Protein Hydrolysate/Xanthan Gum as Fat Replacer in Ice Cream by Combined Enzymatic and Heat-Shearing Treatment".
Lucey, J. A. Milk Proteins (Third Edition), Academic Press, 2020, Chapter 16, pp. 599-632 "Milk protein gels".
McMahon, D. J. et al., Journal of Dairy Science, 1996, 79, 1911-1921, "Use of fat replacers in low fat Mozzarella cheese".
Sirikulchayanont , P. et al. Int. J. Food Prop. 2007, 10(3), 621-630, "Characteristics of Microparticulated Particles from Mung Bean Protein".
Shi D. et al. Food review International 2021, 39, 1309-1332, "Recent Developments in Processing, Functionality, and Food Applications of Microparticulated Proteins".
Spiegel, T. Int J. Food Sci & Tech. 1999, 34(5-6), 523-531 "Whey Protein Aggregation under Shear Conditions-Effects of Lactose and Heating Temperature on Aggregate Size and Structure".
Spiegel , T. et al. Int J. Food Sci & Tech. 2002, 37(5), 559-568 "Whey Protein Aggregation under Shear Conditions—Effects of pH-Value and Removal of Calcium".
Singer, N. S, in Handbook of Fat Replacers; Roller, S., Jones, J.A., Eds .; CRC Press: Boca Raton, 1996; pp. 175-190, "Microparticulated Proteins as Fat Mimetics".
Celigueta Torres, I. et al. International Dairy Journal, vol. 21, Issue 9, 2011, pp. 645-655, "Effect of microparticulated whey protein with varying content of denatured protein on the rheological and sensory characteristics of low-fat yoghurt".

* cited by examiner

*Primary Examiner* — Nikki H. Dees
*Assistant Examiner* — Andrew E Merriam
(74) *Attorney, Agent, or Firm* — BCF LLP

(57) ABSTRACT

The present invention relates to a method for the preparation of a microparticulated rBLG (recombinant β-lactoglobulin), a microparticulated rBLG obtained from said method and a composition thereof, and the use of such microparticulated rBLG for making animal and non-animal dairy products.

13 Claims, 4 Drawing Sheets

H1 H2 H3

S1 S2 S3

MICROPARTICULATION OF RECOMBINANT BETA-LACTOGLOBULIN AND ASSOCIATED FOOD APPLICATIONS

CROSS-REFERENCE TO RELATED APPLICATIONS

This application claims the benefit of priority from European Patent Application No. EP 23 306 688.5, filed on Oct. 2, 2023, which is incorporated by reference herein in its entirety.

FIELD OF INVENTION

The present invention relates to a method for the preparation of a microparticulated rBLG (recombinant β-lactoglobulin), a microparticulated rBLG obtained from said method and a composition thereof, and the use of such microparticulated rBLG for making non animal and animal dairy products.

BACKGROUND OF INVENTION

β-Lactoglobulin (BLG) is a whey protein present in many mammalians milk, and in particular in cow and sheep's milk. Whey proteins have been recognized as a protein source and contains biologically active components potentially beneficial to the human health.

β-Lactoglobulin (BLG) is the major whey protein, accounting for more than 40% of the total whey protein. Bovine β-lactoglobulin (BLG) is a protein of 162 amino acid residues with a molecular weight of 18.4 kDa. Because of its beneficial effects on human health, but also because of its physical properties and intrinsic characteristics, BLG is of direct interest in the food industry. Indeed, the amino acid content in BLG exceeds the Food and Agriculture nutritional intake recommendations both for children aged 2 to 5 and adults.

An alternative to the BLG is the use of recombinant β-lactoglobulin (rBLG) already used in the dairy industry to replace the amino acid intake and providing animal free products.

Native rBLG is commercially available and has the same functional properties such as emulsification, foaming and thermal-gelation as animal whey protein.

However, native rBLG, similarly to native animal whey proteins, are not stable when submitted to a heating step like thermal pasteurization or sterilization found in the food processes. They can prematurely coagulate or form gels during heat treatment and cause severe fouling in the tubes or the plates of the heat exchangers. After being submitted to such heat pasteurization or sterilization, native rBLG are not stable to acidic pH as they coagulate near their isoelectric point. Native rBLG cannot be used either to provide fat-mimetic sensory attribute.

An alternative to the use of native rBLG in the composition of animal free products, is plant-based proteins. In particular, microparticulated plant-based proteins have been developed to reproduce structure and functionality of microparticulated whey proteins (Trends in Food Science & Technology 2020, 106, pages 457-468). However, these microparticulated plant-based proteins suffer from several disadvantages such as low nutritional value, undesired after-taste or poor functional properties as for example solubility or stability against sedimentation, and then are not as efficient as animal whey proteins.

Therefore, there is a need in developing animal-free proteins, and more particularly to develop animal-free protein having characteristics and properties similar to microparticulated whey-proteins, in particular properties regarding the heat stability (thermal pasteurization and/or sterilization), the ability of fat-mimetic sensory attributes or the absence of gelling properties under acidic pH. Also, it would be advantageous that the protein presents an amino-acid profile close to the one of β-lactoglobulin (BLG).

SUMMARY

The present invention relates to a method for the preparation of microparticulated recombinant β-lactoglobulin (rBLG) comprising the steps:

a) Providing an aqueous solution of rBLG, said aqueous solution comprising from 3 to 20% w/w of rBLG and having a pH between 3 and 8, preferably between 4 and 8, b) Heating the aqueous solution of rBLG at a temperature comprised between 75 and 99° C., and c) Applying a high shear rate treatment of at least 70 $s^{-1}$, preferably at least 100 $s^{-1}$, to the aqueous solution of rBLG to afford a microparticulated rBLG aqueous solution, the percentage being expressed in weight in relation to the total weight of the aqueous solution.

In one embodiment, the temperature of the heating step (step b) is comprised between 8° and 99° C., preferably between 82 and 98° C.

In one embodiment, the rBLG concentration in the aqueous solution of step a is comprised between 5 and 15% w/w, preferably between 8 and 20% w/w, the percentage being expressed in weight in relation to the total weight of the aqueous solution.

In one embodiment, the pH of the aqueous solution of step (a) is comprised between 4.5 and 7, preferably 5.5 and 6.5.

In one embodiment, the heating step (step b) and the high shear rate treatment (step c) are performed simultaneously.

In one embodiment, the high shear rate treatment (step c) is performed after the heating step (step b).

In one embodiment, the method of the invention comprises one or more steps selected among: a step of cooling the aqueous solution to a temperature lower than 65° C. (step d), a step of concentrating the aqueous solution (step e), and a step of drying the aqueous solution (step f). In one embodiment, the aqueous solution of step (a) further comprises at least one polysaccharide.

In one embodiment, the rBLG aqueous solution comprises polysaccharides with a polysaccharide/rBLG ratio comprised between 1/3 and 1/30.

In one embodiment, the rBLG is obtained from fungi, preferably from fungi of the genus *Aspergillus.*

Another object of the invention is a microparticulated rBLG obtained from the process.

In one embodiment, the microparticulated rBLG is in the form of aggregates, said aggregates having an average particle size comprised between, 0.1 and 15 μm, preferably between 1 and 10 μm, more preferably between 1 and 6 μm.

Another object of the invention is a dry composition comprising microparticulated rBLG with a microparticulated rBLG content comprised between 45-95% w/w and at least one polysaccharide, the percentage being expressed in weight in relation to the total weight of the dry composition.

In one embodiment, in the dry composition, the microparticulated rBLG is in the form of aggregates, said aggregates having an average particle size comprised between 0.1 and 15 μm, preferably between 1 and 10 μm, more preferably between 1 and 6 μm.

Another object of the invention is an aqueous solution of microparticulated rBLG, the solution comprising from 2 to 20% w/w of microparticulated rBLG, 0.1 to 5% w/w of polysaccharide and water, the percentage being expressed in weight in relation to the total weight of the aqueous solution.

Finally, another object of the invention is the use of microparticulated rBLG, or the use of a dry microparticulated rBLG composition or the use of an aqueous solution of microparticulated rBLG, for making animal and non-animal dairy products.

Definitions

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure in which variations and additions do not depart from the present technology. Hence, the following description is intended to illustrate some particular embodiments of the technology, and no to exhaustively specify all permutations, combinations and variations thereof.

Unless otherwise required by context, the use herein of the singular is to be read to include the plural and vice versa. The term "a" and "an" and "the" similar references as used herein refer to both the singular and the plural, otherwise indicated herein or clearly contradicted by context.

The recitation herein of numerical ranges by endpoints is intended to include all numbers subsumed within that range (e.g., a recitation of 1 to 5 includes 1, 1.25, 1.5, 1.75, 2, 2.45, 2.75, 3, 3.80, 4, 4.32, and 5).

The term "about" is used herein explicitly or not. Every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. For example, the term "about" in the context of a given value or range refers to a value or range that is within 20%, preferably within 15%, more preferably within 10%, more preferably within 9%, more preferably within 8%, more preferably within 7%, more preferably within 6%, and more preferably within 5% of the given value or range.

The expression "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein. The term "or" as used herein should in general be construed non-exclusively. For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

The terms "from . . . to . . . " and "between . . . and . . . " as used herein must be understood as including the boundaries mentioned.

On the contrary, the expressions "greater than . . . ", "more than . . . ", "higher than . . . ", "less than . . . " and "lower than . . . " as used herein do not include the boundaries mentioned.

The abbreviation "% w/w" means weight/weight percent. Other abbreviations can be used to define mass percentage, such as "wt %" (weight percent).

As used herein, the term "comprise" is used in its non-limiting sense to mean that items following the word are included, but items not specifically mentioned are not excluded.

The expression "native protein", as used herein, refers to protein in its natural state with intact structure, i.e. the structure is not altered by chemical or physical treatments. The native state of the protein is its properly folded and assembled structure conferring stability and allowing functional activity.

The term "recombinant protein", as used herein, refers to a protein produced by a genetically modified organism, wherein said organism does not produce said protein unless the genetic modification. The genetically modified organism, or "host" comprises a DNA sequence coding for the protein under control of regulatory elements allowing transcription and translation of said DNA into the recombinant protein.

According to the present technology, the genetically modified organism or host or host cell is modified with a DNA sequence coding for β-lactoglobulin (BLG) and refers to a cell into which a recombinant nucleotide sequence has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host" or "host cell" as used herein.

In some preferred embodiments, BLG can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth BLG.

Advantageously, BLG is bovine BLG. The protein sequence of BLG as well as DNA sequences coding for said BLG are known, disclosed in the website: www.uniprot.org/uniprotkb/P0274/entry.

The expression "denatured protein", as used herein, refers to protein for which the chemical architecture is disrupted. Proteins are highly organized structures having primary, secondary, tertiary and quaternary structures. Any change in the structural arrangement of the secondary, tertiary and/or quaternary structures corresponds to the denaturation of the protein altering its structure and rendering said protein incapable of performing its original assigned function.

The expression "functionalized protein", as used herein, refers to protein that has undergone a treatment to modify its properties via chemical or physical treatment. Methods to functionalize proteins include chemical treatments such as salt washing, chemical hydrolysis and precipitation, and physical treatments such as heat treatment, high/low pressure application, sonication or shearing.

As used herein, the term "microparticulation" refers to the process where proteins, by heat treatment, are denatured and extensively aggregated, and during or after heat treatment the aggregations are divided into smaller particles as a result of mechanical treatment such as a shear treatment.

The expression "microparticulated protein", as used herein, refers to a protein, for example microparticulated rBLG, made according to a microparticulation process, and in particular according to the microparticulation process of the invention.

The expression "room temperature" when used to characterize the temperature of a particular step in a method, refers to the temperature within enclosed space at which reactions can be carried out without device to maintain constant temperature. In some embodiments, a room temperature corresponds to a temperature from 15 to 25° C., preferentially a temperature from 18 to 25° C., and more preferentially from 20 to 25° C.

The expression "room temperature" when used to characterize the properties of a compound, such as "gellable at room temperature", means from 15 to 25° C.

The expression "food product" as used herein refers to a composition that can be ingested by humans or animals, including domesticated animals (e.g., dogs, cats), farm animals (e.g., cows, pigs, horses), and wild animals (e.g., non-domesticated predatory animals). In various embodiments, the food products provided herein meet standards for food safety required by the U.S. Food and Drug Administration (FDA), the U.S. Department of Agriculture, the European Food Safety Authority, and/or other state or region food regulatory agencies. The expression "food product" includes compositions that can be combined with or added to other ingredients to make compositions that can be ingested by humans or animals. According to the invention, examples of food products are dairy products.

The expression "dairy product", also called "animal dairy products", as used herein refers to milk (e.g., whole milk [at least 3.5% milk fat], partly skimmed milk [from 1.5% to 1.8% milk fat], skim milk [less than 0.5% milk fat], cooking milk, condensed milk, flavored milk, goat milk, sheep milk, dried milk, evaporated milk, milk foam), and products derived from milk, including but not limited to yogurt (e.g., whole milk yogurt [at least 6 grams of fat per cup], low-fat yogurt [between 2 and 5 grams of fat per cup], nonfat yogurt [less than 0.5 percent milk fat by weight], Greek yogurt [strained yogurt with whey removed], whipped yogurt, stirred yogurt, goat milk yogurt, Labneh [labne], sheep milk yogurt, yogurt drinks [e.g., whole milk Kefir, low-fat milk Kefir], Lassi), cheese (e.g., whey cheese such as ricotta and mozzarella, semi-soft cheese such as Havarti and Munster, medium-hard cheese such as Swiss and Jarlsberg, hard cheese such as Cheddar and Gouda, soft ripened cheese such as Brie and Camembert, cottage cheese, cream cheese, curd), cream (e.g., whipping cream, coffee whitener, coffee creamer, sour cream, crème fraiche), frozen confections (e.g., ice cream, smoothie, milk shake, frozen yogurt, sundae), fruit preparation, butter, infant formula, weight loss beverages, nutritional beverages, pudding, buttermilk, milk protein concentrate, whey protein concentrate, whey protein isolate, casein concentrate, casein isolate, skim milk powder, whole milk powder, nutritional supplements, texturizing blends, flavoring blends, or coloring blends. The expressions "dairy product" or "animal dairy product" or even "animal product", as used herein, refer to product or dairy product that comprises components of animal origin, or that comprises both components of animal origin and components of non-animal origin.

The expression "high protein dairy product", as used herein, refers to protein enriched product for which the total of protein concentration exceeds 5%, or for which the protein concentration is higher than that of standard products sold on the market and not considered protein rich. Such high protein dairy products are for example (but not limited to) high proteins yogurts, high protein UHT (ultra heat treatment) drinks, high protein fruit preparations, high protein cream cheeses, high proteins snacks, high protein bites, high protein cereal bars, high protein ready to drink milk, high protein milk beverages or high protein beverages.

The expression "non-animal-derived", as used herein, refers to a component (e.g., protein, lipid, carbohydrate) that is not native to an animal cell, like a recombinant protein produced by a microbial host or by a plant cell for instance. In some embodiments, the expression "non-animal-derived" refers to components derived from naturally occurring or modified plants, algae, fungi, or microbes. Similarly, the expressions "non-animal product" and "non-animal dairy products", as used herein, refer to a product or a dairy product that does not comprise component of animal origin.

According to the present invention, "non-animal dairy products", also called "dairy-like products", relate to products that do not comprise milk or milk protein of animal origin. Advantageously, dairy-like products comprise milk of vegetal origin such as plant-based milk, and preferably selected from soy, oat, almond and coconut milk, or proteins extracted from plants, algae, fungi or microbes.

The expression "animal-derived", as used herein, refers to component, such as a milk protein, produced by an animal, for instance, a cow. In some embodiments, the term "animal-derived" refers to a mammal-produced milk or a mammal-produced dairy product.

DETAILED DESCRIPTION

The invention relates to a method for the preparation of microparticulated recombinant β-lactoglobulin (rBLG) comprising the steps of:

a) Providing an aqueous solution of rBLG, said aqueous solution comprising from 3 to 20% w/w of rBLG and having a pH between 3 and 8, preferably between 4 and 8,
b) Heating the aqueous solution of rBLG at a temperature comprised between 75 and 99° C. and
c) Applying a high shear rate treatment of at least 70 $s^{-1}$, preferably at least 100 $s^{-1}$, to the aqueous solution of rBLG, to afford a microparticulated rBLG aqueous solution, the percentage being expressed in weight in relation to the total weight of the aqueous solution.

Recombinant β-Lactoglobulin (rBLG)

Recombinant β-lactoglobulin (rBLG) is obtained via a) culturing a genetically modified organism under conditions suitable for production and/or secretion of the rBLG, and b) isolating said recombinant protein from the culture.

Methods for the production of rBLG are known, and disclosed for example in Food Research International, 2023, 163, 112131, Mol. Biotechnol. 2016, 58, 10, 605-618 and Protein Eng; 1997, 10, 11, pages 1339-1345.

Genetically modified organisms, or host, for the production of rBLG are selected among yeast, bacteria and fungi.

In one embodiment, the host is a yeast strain, and in particular a yeast selected from the strains *Kluyveromyces* sp., *Pichia* sp., *Saccharomyces* sp., *Tetrahymena* sp., *Yarrowia* sp., *Hansenula* sp., *Blastobotrys* sp., *Candida* sp., *Zygosaccharomyces* sp., *Debaryomyces* sp., *Saccharomyces cerevisiae*, and *Pichia pastoris*.

In another embodiment, the host is a bacterial cell. Non limiting examples of bacterial cells suitable for the production of rBLG according to the invention are bacterial cells selected from the species of *Acetobacter suboxydans, Acetobacter xylinum, Actinoplane missouriensis, Bacillus cereus, Bacillus coagulans, Bacillus licheniformis, Bacillus stearothermophilus, Bacillus subtilis, Escherichia coli, Lactobacillus bulgaricus, Lactococcus lactis, Lactococcus lactis* Lancefield Group N, *Leuconostoc citrovorum, Leuconostoc dextranicum, Leuconostoc mesenteroides* strain NRRL B-512 (F), *Micrococcus lysodeikticus, Streptococcus cremoris, Streptococcus lactis, Streptococcus lactis* subspecies *diacetylactis, Streptococcus thermophilus, Streptomyces chattanoogensis, Streptomyces griseus, Streptomyces natalensis, Streptomyces olivaceus, Streptomyces olivochromogenes, Streptomyces rubiginosus*, and *Xanthomonas campestris*. Preferably, the host cell is selected from *Bacillus cereus, Bacillus coagulans, Bacillus licheniformis, Bacillus stearothermophilus* and *Bacillus subtilis*. Advantageously, the host cell is *Bacillus subtilis* when the host is a bacterial cell.

Yet, in another embodiment, the host is selected among fungi, and for example selected among *Aspergillus niger, Aspergillus niger* var. *awamori, Aspergillus oryzae, Candida guilliermondii, Candida lipolytica, Candida pseudotropicalis, Candida utilis, Endothia parasitica, Eremothecium ashbyii*, and *Fusarium moniliforme*.

In preferred embodiments, the fungus is selected among filamentous fungi, and preferably belong to the genus *Aspergillus* and *Trichoderma*. More preferably, the host is selected from *Aspergillus* species, particularly *Aspergillus niger, Aspergillus niger* var. *awamori*, and *Aspergillus oryzae*.

In a particular embodiment, rBLG is isolated form the culture of recombinant filamentous fungi (Microorganisms. 2022, 10, 4, 753, and U.S. Pat. No. 9,924,728), more particularly a recombinant *Aspergillus* specie selected from *Aspergillus niger, Aspergillus niger* var. *awamori* and *Aspergillus oryzae*.

The recombinant β-lactoglobulin (rBLG) protein sequence can be identical or similar to a BLG sequence from cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth. By "similar to a BLG sequence", it is understood that the rBLG protein sequence has a sequence homology of at least 50%, 60%, 70%, 80%, or 90% with said BLG sequence.

Alternatively, the recombinant β-lactoglobulin (rBLG) protein sequence can be a fragment or a variant with at least 70%, 80%, or 90% sequence identity to a BLG sequence from cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth.

In some embodiments, the recombinant β-lactoglobulin (rBLG) can be a blend of different rBLG. In this case, the blend of different rBLG comprises advantageously at least one of a full length rBLG sequence identical to a rBLG sequence from cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth. According to other embodiments, at least one of the rBLG sequence of the blend is a fragment or variant as defined above. Yet, in other embodiments, at least one of the rBLG sequence of the blend is modified, truncated or trimmed relative to a full length rBLG sequence from cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth.

When the recombinant β-lactoglobulin (rBLG) is a blend of different rBLG, it is understood that rBLG can have been produced from different genetically modified organisms. However, the genetically modified organisms, although different, can be in the same cell culture medium (co-culture). The genetically modified organisms can alternatively be in different culture media. Preferably, only one genetically modified organism produces the blend of rBLG.

Preparation of Microparticulated Recombinant β-Lactoglobulin (rBLG)

According to the invention, the method for the preparation of microparticulated rBLG comprises several steps.

Step (a)

The first step, step (a), is to provide an aqueous solution of recombinant β-lactoglobulin (rBLG), said solution comprising from 3 to 20% w/w of rBLG and having a pH of 3 to 8, preferably between 4 to 8.

In one embodiment, the aqueous solution according to the invention is obtained by dissolving native rBLG in water, preferentially in purified water or demineralized water.

Advantageously, the dissolution of native rBLG is achieved at a temperature comprised between 1 and 60° C., preferably at a temperature comprised between 1° and 50° C., more preferably at a temperature comprised between 15 and 40° C. In a preferred embodiment, the dissolution of native rBLG in water is achieved at room temperature, i.e. at a temperature comprised between 15 and 25° C.

Advantageously, the native rBLG to be dissolved is a purified dehydrated rBLG. Such rBLG proteins can be obtained by culturing a genetically modified organism and isolating said recombinant protein or can be purchased.

In another embodiment, the aqueous solution of rBLG is the liquid solution obtained from the rBLG purification process after fermentation. In other words, the aqueous solution of rBLG is the liquid solution obtained from the downstream process. Thus, according to this embodiment, the aqueous solution of rBLG is preferably the retentate of the ultrafiltration process, that is to say the retentate obtained after concentration and diafiltration.

The aqueous solution according to the invention comprises from 3 to 20% w/w of rBLG, preferably from 5 to 20% w/w of rBLG, more preferably from 5 to 18% w/w of rBLG, or even more preferably from 5 to 16% w/w of rBLG, and still better from 5 to 15% w/w of rBLG, or from 8 to 15% w/w of rBLG, the percentage being expressed in weight in relation to the total weight of the aqueous solution.

Advantageously, the aqueous solution of rBLG comprises from 3 to 15% w/w of rBLG, more preferably from 3 to 12% w/w, of rBLG the percentage being expressed in weight in relation to the total weight of the aqueous solution.

Preferably, the aqueous solution of rBLG comprised from 5 to 12% w/w of rBLG, more preferably from 6 to 11% w/w of rBLG, and even more preferably from 8 to 10% w/w of rBLG, the percentage being expressed in weight in relation to the total weight of the aqueous solution.

The person of ordinary skill in the art knows to determine the required quantity of rBLG to afford such concentration depending on the purity of the rBLG and the volume of the solution.

The pH of the aqueous solution is of importance, and has to be maintained between 3 and 8, and preferably between 4 and 8.

In one embodiment, the pH of the rBLG aqueous solution is higher or equal to 3, preferably higher or equal to 4, more preferably higher or equal to 5 and or higher or equal to 6.

In another embodiment, the pH of the aqueous solution of rBLG is preferably lower than 8, and preferably lower or equal to 7.

Yet in other embodiments, the pH of the rBLG aqueous solution is preferably comprised between 3 and 8, preferably between 4 and 7, more preferably between 4.5 and 6.5, even more preferably between 4.5 and 6, better still between 5 and 6. Advantageously, the pH of the rBLG aqueous solution is around 4.5, around 5.5 or around 6.5.

pH adjustment of the aqueous solution is performed according to known technics in the art, particularly via the addition of acids or bases into said solution. It is understood that acids and bases can be added in the form of an aqueous solution or in the form of salts. Examples of acids and bases that can be used to adjust the pH of the aqueous solution comprising rBLG according to the invention are acidic acid, adipic acid, ammonium aluminum sulphate, ammonium bicarbonate, ammonium carbonate, ammonium citrate dibasic, ammonium citrate monobasic, ammonium hydroxide, ammonium phosphate dibasic, ammonium sulphate monobasic, calcium acetate, calcium acid pyrophosphate, calcium carbonate, calcium chloride, calcium citrate, calcium fumarate, calcium gluconate, calcium hydroxide, calcium lactate, calcium oxide, calcium phosphate dibasic, calcium phosphate monobasic, calcium phosphate tribasic, calcium sulphate, carbon dioxide, citric acid, cream of tartar, fumaric acid, gluconic acid, glucono-delta-lactone, hydrochloric acid, lactic acid, magnesium carbonate, magnesium citrate, magnesium fumarate, magnesium hydroxide, magnesium oxide, magnesium phosphate, magnesium sulphate, malic acid, manganese sulphate, metatartaric acid, phosphoric acid, potassium acid tartrate, potassium aluminum sulphate, potassium bicarbonate, potassium carbonate, potassium chloride, potassium citrate, potassium fumarate, potassium hydroxide, potassium lactate, potassium phosphate dibasic, potassium phosphate tribasic, potassium pyrophosphate tetrabasic, potassium sulphate, potassium tartrate, potassium tripolyphosphate, sodium acetate, sodium acid pyrophosphate, sodium acid tartrate, sodium aluminum phosphate, sodium aluminum sulphate, sodium bicarbonate, sodium bisulphate, sodium carbonate, sodium citrate, sodium fumarate, sodium gluconate, sodium hexametaphosphate, sodium hydroxide, sodium lactate, sodium phosphate dibasic, sodium phosphate monobasic, sodium phosphate tribasic, sodium potassium hexametaphosphate, sodium potassium tartrate, sodium potassium tripolyphosphate, sodium pyrophosphate tetrabasic, sodium tripolyphosphate, sulphuric acid, sulphurous acid, and tartaric acid. In a preferred embodiment, the pH of the aqueous solution comprising rBLG is adjusted via the addition of an aqueous solution of hydrochloric acid.

The aqueous solution comprising rBLG can further comprise one or more polysaccharides. According to the invention, the term "polysaccharides" refers to linear or branched polymers composed of monosaccharide units linked by glycosidic bonds. Monosaccharides have general formula $(CH_2O)_n$ with n the number of monosaccharides and being of at least three. Examples of monosaccharides are trioses, tetroses, pentoses, hexoses, heptoses. Particularly, polysaccharides are polymers of galactose, glucose, mannose in different proportions. Polysaccharides are preferably polymers of natural origin, and in particular produced by plants, fungi, yeasts or bacteria, possibly modified during or after extraction form the producing organism.

According to some embodiments, the aqueous solution comprising rBLG does not comprise a polysaccharide.

According to some other embodiments, the aqueous solution comprising rBLG may further comprise at least one polysaccharide.

When it is present, the polysaccharide is advantageously of fungal origin, and preferably is isolated from a filamentous fungi selected from the group of species of *Aspergillus* and *Trichoderma*.

In another embodiment, the polysaccharide is produced by the same organism as the genetically modified organism producing the rBLG as defined above.

Yet, in another embodiment, the polysaccharide and rBLG are obtained as a mixture when isolating rBLG from the culture of the genetically modified organism producing rBLG as defined above.

In one preferred embodiment, polysaccharides, when they are present in the aqueous solution of rBLG, are heteropolysaccharides. Preferably, heteropolysaccharides comprise galactose and mannose, analysis of heteropolysaccharides having been performed by spectrophotometry and chromatography after hydrolysis of said heteropolysaccharides. Advantageously, the mannose/galactose ratio in polysaccharides, when they are present in the aqueous solution of rBLG, ranges from 0.5/1 to 5/1, preferably from 0.5/1 to 4/1, more preferably from 1/1 to 3/1, or more preferably from 1/1 to 2/1, and still better from 1.5/1 to 2/1.

In another preferred embodiment, polysaccharides, when they are present in the aqueous solution of rBLG, comprise heteropolysaccharides as defined above, and further comprise glucose. Advantageously, when present, the glucose can be found in a free form or in the form of β-glucan.

The glucose content, when present, can be determined by spectrophotometry and chromatography, optionally after hydrolysis of β-glucan. Advantageously, the glucose content in polysaccharides, when they are present in the aqueous solution of rBLG, is lower than 30% w/w in relation to the total weight of polysaccharides, preferably lower than 25% w/w and more preferably lower than 20% w/w in relation to the total weight of polysaccharides. Preferably, when present, the glucose content is comprised between 0.001 and 20% w/w in relation to the total weight of polysaccharides, preferably between 0.01 and 18% w/w, more preferably between 0.5 and 16% w/w, even more preferably between 1 and 15% w/w in relation to the total weight of polysaccharides. Yet, when present, the glucose content in polysaccharides is comprised between 3 and 15% w/w, more preferably between 5 and 15% w/w, even more preferably between 8 and 14% w/w in relation to the total weight of polysaccharides.

The aqueous solution of rBLG can comprise one or more polysaccharides. Preferably, the polysaccharide content in the aqueous solution of rBLG ranges from 0 to 50% w/w, the percentage being expressed in relation to the dry matter of the aqueous solution.

In one embodiment, the polysaccharide content in the aqueous solution is preferably lower than 40% w/w, more preferably lower than 30% w/w, and better lower than 20% w/w, the percentage being expressed in relation to the dry matter of the aqueous solution.

Advantageously, the aqueous solution of rBLG comprises between 0 and 30% w/w of polysaccharides, preferably between 0 and 20% w/w, more preferably between 0 and 15% w/w, and more preferably between 0 and 10% w/w, the percentage being expressed in relation to the dry matter of the aqueous solution.

In one preferred embodiment, the polysaccharide content in the aqueous solution comprising rBLG is comprised between 0.01 and 8% w/w, preferably between 0.05 and 6% w/w, and more preferably between 0.1 and 5% w/w, the percentage being expressed in relation to the dry matter of the aqueous solution.

The content of polysaccharide in the aqueous solution comprising rBLG can also be defined as a polysaccharide/rBLG ratio.

In one embodiment, the polysaccharide/rBLG ratio is lower than or equal to 1/2, and preferably lower than or equal to 1/3.

Advantageously, when the aqueous solution comprises rBLG and one or more polysaccharides, the polysaccharide/rBLG ratio ranges from 1/30 to 1/2, preferably from 1/25 to 1/2, more preferably from 1/25 to 1/3, even more preferably from 1/20 to 1/2. In preferred embodiments, the polysaccharide/rBLG ratio ranges from 1/20 to 1/3, preferably from 1/15 to 1/3, more preferably from 1/10 to 1/3.

Advantageously, when the aqueous solution comprises rBLG and one or more polysaccharides, the polysaccharide/rBLG ratio is of around 1/6, around 1/5 or around 1/4.

Additional elements can be present in the aqueous solution of rBLG. Mention can be made of minerals such as copper, calcium, iron, magnesium, phosphor, and potassium. Minerals found in the aqueous solution of rBLG can be residues from the isolation of rBLG from the culture of the genetically modified organism producing the rBLG.

In some embodiments, minerals can be added to the aqueous solution comprising rBLG. Preferably, minerals added to the aqueous solution comprising rBLG are selected among divalent ions, and more preferably are selected among divalent cations such as barium, copper, calcium, magnesium, manganese, zinc, iron, nickel, cobalt, tin, cadmium, lead, sodium, potassium, and phosphorus and mixtures thereof. More preferably, when added, the divalent ions are calcium ions.

In one preferred embodiment the rBLG aqueous solution comprises calcium ions and more particularly calcium ions selected among calcium chloride, calcium lactate and calcium phosphate and mixtures thereof.

Advantageously, when minerals are present in the rBLG aqueous solution, the concentration in minerals is lower than 5% w/w, preferably lower than 2.5% w/w, and more preferably lower than 2% w/w, the percentage being expressed in weight in relation to the dry matter of the aqueous solution.

In some preferred embodiments, and when minerals are present in the rBLG aqueous solution, the concentration in minerals is comprised between 0 and 5% w/w, preferably between 0.01 and 5% w/w, more preferably between 0.01 and 2.5% w/w, even more preferably between 0.01 and 2% w/w, and still better between 0.01 and 1% w/w, the percentage being expressed in weight in relation to the dry matter of the aqueous solution. Advantageously, the concentration in minerals in the rBLG aqueous solution is comprised between 0.01 and 0.5% w/w, the percentage being expressed in weight in relation to the dry matter of the aqueous solution.

In some embodiments, the composition of the aqueous solution comprising rBLG also comprises one or more polysaccharides and minerals.

According to these embodiments, the rBLG aqueous solution comprises:

From 50 to 99% w/w of rBLG,

From 0 to 30% w/w of polysaccharide, and

From 0 to 10% w/w of minerals, the percentage being expressed in weight in relation to the total weight of dry matter of the aqueous solution.

In another preferred embodiment, the rBLG aqueous solution comprises:

From 60 to 99% w/w of rBLG,

From 0 to 25% w/w of polysaccharide, and

From 0 to 5% w/w of minerals, the percentage being expressed in weight in relation to the total weight of dry matter of the aqueous solution.

In another preferred embodiment, the rBLG aqueous solution comprises:

From 70 to 99% w/w of rBLG,

From 5 to 20% w/w of polysaccharide, and

From 0 to 5% w/w of minerals, the percentage being expressed in weight in relation to the total weight of dry matter of the aqueous solution.

Step (b)

Following the preparation of the aqueous solution comprising recombinant β-lactoglobulin (rBLG) as defined above, a heating step is performed (step b) to afford denatured rBLG. The aqueous solution is therefore heated at a temperature comprised between 75 and 99° C.

The heat treatment (step b) is preferably carried out at a temperature higher or equal to the denaturation temperature of said rBLG.

In one embodiment, the temperature of the heat treatment is lower than or equal to 99° C., and even more preferably lower than or equal to 95° C.

In another embodiment, the temperature of the heat treatment (step b) is higher than or equal to 75° C., preferably higher than or equal to 80° C., and more preferably higher than or equal to 85° C.

Preferably, the temperature of the heating step (step b) is comprised between 75 and 99° C., preferably between 77 and 99° C., more preferably between 8° and 99° C., even more preferably between 82 and 99° C., or preferably between 82 and 98° C., and more preferably between 83 and 95° C., or even more preferably between 85 and 92° C., or preferably between 87 and 92° C., and still better between 88 and 91° C.

Advantageously, the heat treatment of step (b) is carried out at a temperature around 90° C.

In one preferred embodiment, the heating step (b) is carried out at a temperature of around 80° C., and the concentration of the rBLG aqueous solution is of 10% w/w and at pH 6, the percentage being expressed in weight in relation to the total weight of the aqueous solution.

In one preferred embodiment, the heating step (b) is carried out at temperature of 82° C. or higher, and the concentration of rBLG in the aqueous solution is comprised between 3 and 15% w/w and the pH is comprised between 4.5 and 6.5, the percentage being expressed in weight in relation to the total weight of the aqueous solution.

In one preferred embodiment, the heating step is carried out at temperature of 90° C. or higher, and the concentration of rBLG in the aqueous solution is comprised between 3 and 15% w/w and the pH is comprised between 4.5 and 6.5, the percentage being expressed in weight in relation to the total weight of the aqueous solution.

In one preferred embodiment, the heat treatment of step (b) is carried out at a temperature of 75 to 95° C. and the concentration of rBLG in the aqueous solution ranges from 3 to 20% w/w, the pH of the aqueous solution being between 3 and 8, preferably between 4 and 8, the percentage being expressed in weight in relation to the total weight of the aqueous solution.

Still in another preferred embodiment, the heat treatment of step (b) is carried out at a temperature of 75 to 95° C. and the concentration of rBLG in the aqueous solution ranges from 3 to 16% w/w, the pH of the aqueous solution being between 3 and 8, preferably between 4 and 8, the percentage being expressed in weight in relation to the total weight of the aqueous solution.

Preferably, the heat treatment of step (b) is carried out at a temperature of 80 to 95° C. and the concentration of rBLG in the aqueous solution ranges from 3 to 16% w/w, the pH of the aqueous solution being between 3 and 8, preferably between 4 and 8, the percentage being expressed in weight in relation to the total weight of the aqueous solution.

Advantageously the heat treatment of step (b) is carried out at a temperature of 80 to 90° C. and the concentration of rBLG in the aqueous solution ranges from 5 to 15% w/w, the pH of the aqueous solution being between 3 and 8, preferably between 4 and 8, the percentage being expressed in weight in relation to the total weight of the aqueous solution.

More advantageously the heat treatment of step (b) is carried out at a temperature of 80 to 90° C. and the concentration of rBLG in the aqueous solution ranges from 5 to 15% w/w, the pH of the aqueous solution being between 4 and 7, the percentage being expressed in weight in relation to the total weight of the aqueous solution.

Heat treatment of the aqueous solution comprising rBLG lasts for several seconds, several minutes or even several hours. Overall, heat treatment of the rBLG aqueous solution according to the invention lasts for from 1 second to 90 minutes.

In one embodiment, the heat treatment of the rBLG aqueous solution is carried out for at least 1 second, at least 10 seconds, or preferably at least 30 seconds.

In another embodiment, the heat treatment of the rBLG aqueous solution is carried out for less than 90 minutes, preferably less than 60 minutes and more preferably less than 30 minutes.

In other embodiments, the heat treatment of the rBLG aqueous solution is carried out for 10 seconds to 90 minutes, preferably for 30 seconds to 90 minutes and more preferably for 1 to 90 minutes. Advantageously, the heat treatment is carried out for a period of time comprised between 2 and 75 minutes, preferably between 5 and 60 minutes, more preferably between 5 and 50 minutes and even more preferably between 10 and 45 minutes. Advantageously, the aqueous solution of rBLG is heated during 10 and 30 minutes, preferably during 15 and 30 minutes, more preferably during 15 and 25 minutes. In a preferred embodiment, the heat treatment is of around 20 minutes.

During the heat treatment, the aqueous solution of rBLG is advantageously stirred under moderate agitation, and more particularly at a rotational speed of 1 to 1000 rpm (rotation par minute) when the method is carried out in batch. In this case, the stirring is achieved for example by using rotating blade or magnetic stirrer. It is understood that the person of ordinary skill in the art will know what is the appropriate stirring method to afford the desired rotational speed depending on the container and the volume of the aqueous solution.

In one embodiment, the rotational speed is of 10 to 1000 rpm, preferably of 50 to 1000 rpm, more preferably of 100 to 1000 rpm. Preferably, the rotational speed during the heat treatment is of 50 to 900 rpm, preferably of 50 to 700 rpm, more preferably of 100 to 500 rpm, even more preferably of 100 to 400 rpm, or more preferably of 100 to 300 rpm when the method is performed in batch.

The rotational speed can also define as a peripheral speed. Peripheral speed is defined by the linear velocity of the propeller at the end of the blade. According to this embodiment, the peripheral speed is preferably between 0.5 and 20 m/s, more preferably between 1 and 18 m/s, more preferably between 2 and 15 m/s, even more preferably between 5 and 12 m/s, and still better between 7 and 10 m/s.

In some embodiments, the heat treatment can be carried out following a continuous process. This is notably the case when high quantity of rBLG is handled at technical scale. According to the invention, technical scale means above 1 kg of rBLG processed per hour. When the heat treatment is a continuous process, plate heat exchangers and/or tubular heat exchangers can be used and the time of the reaction corresponds to the residence time holding tubes. The person of ordinary skills in the art is familiar with the continuous process and will be able to define the appropriate heat apparatus as well as the reaction time.

The two-step sequence, step (a) of providing an aqueous solution of rBLG and step (b) of heating said rBLG aqueous solution allows the formation of denatured rBLG.

Step (c)

In addition to the two-step sequence, the method of the invention further comprises a step (c) of applying a high shear rate treatment to the aqueous solution comprising rBLG leading to the formation of microparticulated rBLG.

According to the invention, high shear rate treatment (also called high shear treatment) can be performed by using stirring apparatus such as stirred vessels, agitators, static mixers, and rotor-stator mixers, or homogenizers, or hydrodynamic cavitation reactors. Examples of high shear mixer are rheometer with coaxial cylinder geometry for a use at a laboratory scale or scraped surface heat exchanger reactors for a use at a technical scale.

In some embodiments, the high shear rate treatment is performed using a stirring apparatus, wherein a high shear rate can be applied to the aqueous solution of rBLG. The person of ordinary skill in the art is familiar with such apparatus and will be able to choose the appropriate apparatus depending on the characteristics and properties of the aqueous solution.

Advantageously, the high shear rate treatment is carried out with a shear rate of at least 70 $s^{-1}$, preferably at least 100 $s^{-1}$.

Preferably, the high shear rate treatment is carried out with a shear rate lower than or equal to 3000 $s^{-1}$, preferably lower than or equal to 2500 $s^{-1}$ and more preferably lower than or equal to 2000 $s^{-1}$.

Yet in preferred embodiment, the high shear rate treatment is carried out with a shear rate comprised between 70 and 3000 $s^{-1}$, preferably between 100 and 3000 $s^{-1}$, more preferably between 100 and 2800 $s^{-1}$, even more preferably between 100 and 2500 $s^{-1}$, and still better between 100 and 2500 $s^{-1}$. Preferably, the shear rate of the high shear rate treatment is comprised between 100 and 2200 $s^{-1}$, preferably between 100 and 2000 $s^{-1}$, more preferably between 100 and 1500 $s^{-1}$, even more preferably between 100 and 1200 $s^{-1}$, and even more preferably between 100 and 1000 $s^{-1}$. Still better, the high shear rate treatment is carried out at a shear rate comprised between 100 and 800 $s^{-1}$, preferably between 100 and 700 $s^{-1}$, more preferably between 200 and 700 $s^{-1}$, even more preferably between 300 and 600 $s^{-1}$ The shear rate is preferably around 100 $s^{-1}$, around 200 $s^{-1}$, 300 $s^{-1}$, around 400 $s^{-1}$, around 500 $s^{-1}$ or around 600 $s^{-1}$.

In one preferred embodiment, the high shear rate treatment is performed in a stirring apparatus as previously defined and a shear rate as defined above, preferably comprised between 70 and 3000, or between 100 and 3000 $s^{-1}$, is applied.

In one embodiment, the high shear rate treatment is performed using a homogenizer, and preferably a high-pressure homogenizer When the high shear rate treatment is performed with a homogenizer, the high-pressure homogenization is conducted at a pressure comprised between 30 and 300 bars, preferably between 30 and 250 bars, more preferably between 50 and 250 bars, or preferably between 50 and 200 bars, even more preferably between 100 and 250 bars, or even more preferably between 50 and 150 bars.

In a preferred embodiment, the high shear rate treatment is carried out in a high-pressure homogenizer with a pressure comprised between 30 and 300 bars.

The high shear rate treatment is carried out for at least 1 second, preferably at least 2 seconds and more preferably at least 5 seconds. However, the reaction time of the shear treatment is lower than or equal to 60 minutes, preferably lower than or equal to 45 minutes.

In one embodiment, the high shear rate treatment lasts from 30 seconds to 45 minutes, preferably from 1 minutes to 40 minutes, more preferably from 1 to 30 minutes, more preferably from 2 to 25 minutes, more preferably from 3 to 20 minutes, or even more preferably from 5 to 15 minutes.

The high shear rate treatment can be performed simultaneously or subsequently to the heating step.

In one embodiment, the high shear rate treatment is carried out simultaneously to the heating step. These steps are then performed at the same time.

When the high shear rate treatment and the heating step are simultaneous, the temperature of the shear treatment is the one of the heating step, as defined above. Preferably, the temperature is comprised between 75 and 99° C., preferably between 75 and 95° C., more preferably between 75 and 92° C., and even more preferably between 78 and 92° C., and still between 8° and 90° C.

When the high shear rate treatment and the heating step are performed simultaneously, the reaction time of the shear treatment can be higher or lower than the reaction time of the heating step. It is then understood that high shear rate treatment of the rBLG aqueous solution can be continued even if the heating steps has ended. Alternatively, it is understood that the high shear rate treatment can last less time than the heating step, and then the rBLG aqueous solution is still heated while the high shear treatment is ended. Alternatively, both the heating step and the high shear treatment can have the same reaction time, and therefore started and ended simultaneously.

In another embodiment, the high shear rate treatment and the heating step are performed independently from each other, the high shear rate treatment being preferably performed after the heating step.

When the high shear rate treatment is applied to the aqueous solution subsequently to the heating step, it is preferably performed in a high-pressure homogenizer. According to this embodiment, high pressure homogenization is preferably conducted at temperature equal to or lower than 70° C., preferably equal to or lower than 65° C., or more preferably equal to or lower than 60° C. Preferably, high-pressure homogenization is conducted at a temperature comprised between 1 and 50° C., preferably between 5 and 50° C., more preferably between 1° and 45° C., or more preferably between 1° and 40° C., even more preferably between 15 and 35° C., and even more preferably between 15 and 30° C. Advantageously, the temperature of the high pressure homogenization is comprised between 15 and 25° C., or between 18 and 22° C.

In another preferred embodiment, the high shear treatment rate is applied by hydrodynamic cavitation.

The three-steps sequence comprising the preparation of a rBLG aqueous solution (step a), said solution comprising from 3 to 20% w/w of rBLG and having a pH of 3 to 8, preferably from 4 to 8, heating the rBLG aqueous solution at a temperature comprised between 75 and 99° C., or preferably between 8° and 99° C. (step b), and applying a high shear rate treatment of at least 70 $s^{-1}$, preferably at least 100 $s^{-1}$ to the aqueous solution simultaneously or subsequently to the heating step (step c), provided microparticulated rBLG.

Additional Steps

The rBLG aqueous solution or microparticulated rBLG aqueous solution can further undergo several treatments such as a cooling step (step d) and/or a concentration step (step e) and/or a drying step (step f).

Step (d)

The method for the preparation of microparticulated rBLG according to the invention can further comprise an additional step d) of cooling the aqueous solution, preferably at a temperature equal to or lower than 70° C.

In one embodiment, the aqueous solution comprising rBLG or microparticulated rBLG is cooled to a temperature equal to or lower than 70° C., preferably equal to or lower than 65° C., and more preferably equal to or lower than 60° C. Preferably, the aqueous solution is cooled to a temperature comprised between 1 and of 55° C., preferably between 1 and 50° C., more preferably between 1 and 45° C., or more preferably between 1 and 40° C., or even more preferably between 1 and 35° C. Advantageously, the aqueous solution is cooled to a temperature comprised between 2 and 30° C., preferably between 5 and 25° C., and more preferably between 5 and 20° C., and even more preferably between 5 and 15° C.

The cooling step can be performed at any stage of the method.

In some preferred embodiments, the cooling step is performed after the heat treatment or after the high shear rate treatment. In other preferred embodiments, the cooling step is performed after the heat treatment and after the high shear rate treatment. Still, in other preferred embodiments, the cooling step is performed after the heat treatment and after the high shear rate treatment, the two steps being conducted simultaneously.

The cooling step can be performed under no or moderate agitation, or under stirring with a high shear rate as previously defined.

Preferably, the cooling step is performed with no stirring.

In another preferred embodiment, the cooling step is performed with moderate agitation, that is to say with a string ranging from 1 to 1000 rpm, preferably from 50 to 1000 rpm, preferably from 50 to 800 rpm, and more preferably from 100 to 800 rpm, more preferably from 100 to 600 rpm, more preferably from 200 to 600 rpm.

Yet, in another preferred embodiment, the cooling step is performed under stirring with a high shear rate, the shear rate being preferably of at least 70 $s^{-1}$, more preferably of at least 100 $s^{-1}$.

Advantageously, the cooling step is performed under stirring with a shear rate comprised between 100 $s^{-1}$ and 3000 $s^{-1}$ and as previously defined.

Step (e)

The aqueous solution comprising rBLG or microparticulated rBLG can also be concentrated (step e). Concentration of the aqueous solution is performed according to the well-known methods of the technical field. Such methods include centrifugation, dialysis, precipitation or salting out, filtration or chromatography. The person of ordinary skill in the art will be able to choose the appropriate method and to apply the appropriate conditions.

Concentration of the aqueous solution can be performed at any stage of the method if needed. However, the concentration step is preferably performed after the three-step sequence of providing an aqueous solution of microparticulated rBLG, i.e. after the step of providing an aqueous solution of rBLG (step a), heating the aqueous solution (step b), and applying a high shear rate treatment to the aqueous solution (step c), and optionally cooling the aqueous solution (step d).

Step (f)

The method of the invention can further comprise a step of drying (step f).

Suitable drying methods are for examples freeze-drying, spray drying and supercritical drying. The person of ordinary skill in the art will know to choose the drying method of choice and suitable parameters to afford the dry microparticulated rBLG without altering the protein properties.

The drying step is preferably performed at the end of the method to afford a dry microparticulated rBLG or a dry microparticulated rBLG composition.

Steps of cooling (step d), concentrating (step e) and drying (step f) the aqueous solution comprising rBLG are optional and can be performed independently of each other.

It should be noted that when performed, steps of cooling (step d), concentrating (step e) and drying (step f) are preferably done after the preparation of the microparticulated rBLG, i.e after steps (a), (b) and/or (c).

Modes of Carrying the Invention

Advantageously, the method for the preparation of microparticulated rBLG comprises the steps of:

a) Providing an aqueous solution of rBLG, said aqueous solution comprising from 3 to 20% w/w of rBLG and having a pH between 3 and 8, preferably between 4 and 8, b) Heating the aqueous solution of rBLG at a temperature comprised between 75 and 99° C., preferably between 82 and 98° C., for 1 second to 90 minutes, and c) Applying to the aqueous solution of rBLG a high shear rate treatment of at least 70 $s^{-1}$, preferably at least 100 $s^{-1}$ to the aqueous solution of rBLG., the percentage being expressed in weight in relation to the total weight of the aqueous solution.

According to a preferred embodiment, the method for the preparation of microparticulated rBLG comprises the steps of:

a) Providing an aqueous solution of rBLG, said aqueous solution comprising from 3 to 20% w/w of rBLG and having a pH between 4 and 6, b) Heating the aqueous solution of rBLG at a temperature comprised between 75 and 99° C., preferably from 82 to 98° C., for 10 to 30 minutes, and c) Applying to the aqueous solution of rBLG a high shear rate treatment of at least 70 $s^{-1}$, preferably at least 100 $s^{-1}$ to the aqueous solution of rBLG., the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 3 to 20% w/w of rBLG and having a pH between 4 and 6, b) Heating the aqueous solution of rBLG at a temperature comprised between 75 and 99° C., preferably between 82 and 98° C., for 1 second to 90 minutes, and c) Applying to the aqueous solution of rBLG a high shear rate treatment, the shear rate being comprised between 70 to 3000 $s^{-1}$, preferably between 100 and 3000 $s^{-1}$, the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 3 to 20% w/w of rBLG and having a pH between 4 and 6, b) Heating the aqueous solution of rBLG at a temperature comprised between 75 and 99° C., preferably between 82 and 98° C., for 1 second to 90 minutes, and c) Applying simultaneously to the aqueous solution of rBLG a high shear rate treatment, preferably with a shear rate of 100 and 1000 $s^{-1}$, the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 8 to 20% w/w of rBLG and having a pH between 5 and 6.5, b) Heating the aqueous solution of rBLG at a temperature comprised between 75 and 99° C., for 1 seconds to 90 minutes, and c) Applying simultaneously to the aqueous solution of rBLG a high shear rate treatment, preferably with a shear rate of 70 to 3000 $s^{-1}$, more preferably with a shear rate of 100 and 3000 $s^{-1}$, the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 3 to 20% w/w of rBLG and having a pH between 5 and 8, b) Heating the aqueous solution of rBLG at a temperature comprised between 82 and 98° C., for 1 seconds to 90 minutes, and c) Applying simultaneously to the aqueous solution of rBLG a high shear rate treatment, preferably with a shear rate of 70 to 3000 $s^{-1}$, more preferably with a shear rate of 100 and 3000 $s^{-1}$, the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 3 to 20% w/w of rBLG and having a pH between 5 and 8, b) Heating the aqueous solution of rBLG at a temperature comprised between 85 and 92° C., 1 seconds to 90 minutes, and c) Applying simultaneously to the aqueous solution of rBLG a high shear rate treatment, preferably with a shear rate of 70 to 3000 $s^{-1}$, more preferably with a shear rate of 100 and 3000 $s^{-1}$, the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 3 to 20% w/w of rBLG and having a pH between 4 and 6, b) Heating the aqueous solution of rBLG at a temperature comprised between 75 and 99° C., for 1 seconds to 90 minutes, c) Applying simultaneously to the aqueous solution of rBLG a high shear rate treatment, preferably with a shear rate of 70 to 3000 $s^{-1}$, more preferably with a shear rate of 100 and 3000 $s^{-1}$, and d) Cooling the microparticulated rBLG aqueous solution, preferably at a temperature equal to or below 70° C., the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 3 to 20% w/w of rBLG and having a pH between 4 and 8, b) Heating the aqueous solution of rBLG at a temperature comprised between 75 and 99° C., for 1 second to 90 minutes, and c) Applying to the aqueous solution of rBLG a high shear rate treatment of 70 to 3000 $s^{-1}$, more preferably with a shear rate of 100 and 3000 $s^{-1}$, subsequently to the heating step the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 3 to 20% w/w of rBLG and having a pH between 4 and 8, b) Heating the aqueous solution of rBLG at a temperature comprised between 75 and 99° C., for 1 second to 90 minutes, d) Cooling the heated aqueous solution of rBLG, preferably at a temperature equal to or below 70° C., and c) Applying to the aqueous solution of rBLG a high shear rate treatment, preferably with a shear rate comprised between 70 and 3000 $s^{-1}$, more preferably with a shear rate of 100 and 3000 $s^{-1}$, the percentage being expressed in weight in relation to the total weight of the aqueous solution.

Advantageously, the method for the preparation of microparticulated rBLG comprises the steps of:

a) Providing an aqueous solution of rBLG, said aqueous solution comprising from 3 to 20% w/w of rBLG and having a pH between 3 and 8, preferably between 4 and 8, b) Heating the aqueous solution of rBLG at a temperature comprised between 75 and 99° C., preferably between 75 and 95° C., for 1 to 90 minutes, and c) Applying to the aqueous solution of rBLG a high shear rate treatment of at least 70 $s^{-1}$, preferably at least 100 $s^{-1}$, the percentage being expressed in weight in relation to the total weight of the aqueous solution.

According to a preferred embodiment, the method for the preparation of microparticulated rBLG comprises the steps of:

a) Providing an aqueous solution of rBLG, said aqueous solution comprising from 3 to 20% w/w of rBLG and having a pH between 4 and 6, b) Heating the aqueous solution of rBLG at a temperature comprised between 75 and 99° C., preferably from 75 to 95° C., for 10 to 90 minutes, and c) Applying to the aqueous solution of rBLG a high shear rate treatment of at least 70 $s^{-1}$, preferably at least 100 $s^{-1}$, the percentage being expressed in weight in relation to the total weight of the aqueous solution According to another preferred embodiment, the method for the preparation of microparticulated rBLG comprises the steps of:

a) Providing an aqueous solution of rBLG, said aqueous solution comprising from 3 to 20% w/w of rBLG and having a pH between 4 and 6, b) Heating the aqueous solution of rBLG at a temperature comprised between 75 and 99° C., preferably between 75 and 95° C., for 1 to 60 minutes, and c) Applying to the aqueous solution of rBLG a high shear rate treatment of at least 70 $s^{-1}$, preferably at least 100 $s^{-1}$, the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 3 to 20% w/w of rBLG and having a pH between 4 and 6, b) Heating the aqueous solution of rBLG at a temperature comprised between 75 and 99° C., preferably between 75 and 95° C., for 1 to 60 minutes, and c) Applying simultaneously to the aqueous solution of rBLG a high shear rate treatment of at least 70 $s^{-1}$, preferably at least 100 $s^{-1}$, the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 3 to 15% w/w of rBLG and having a pH between 4 and 6, b) Heating the aqueous solution of rBLG at a temperature comprised between 75 and 99° C., preferably between 8° and 90° C., for 1 to 60 minutes, and c) Applying simultaneously to the aqueous solution of rBLG a high shear rate treatment of at least 70 $s^{-1}$, preferably at least 100 $s^{-1}$, the percentage being expressed in weight in relation to the total weight of the aqueous solution.

Still, according to a preferred embodiment, the method for the preparation of microparticulated rBLG comprises the steps of:

a) Providing an aqueous solution of rBLG, said aqueous solution comprising from 3 to 15% w/w of rBLG and having a pH between 4 and 6, b) Heating the aqueous solution of rBLG at a temperature comprised between 75 and 99° C., preferably between 8° and 90° C., for 5 to 30 minutes, and c) Applying simultaneously to the aqueous solution of rBLG a high shear rate treatment of 70 to 3000 $s^{-1}$, preferably of 100 to 3000 $s^{-1}$, the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 5 to 10% w/w of rBLG and having a pH between 4 and 6, b) Heating the aqueous solution of rBLG at a temperature comprised between 8° and 90° C., for 5 to 30 minutes, c) Applying simultaneously to the aqueous solution of rBLG a high shear rate treatment of 70 to 3000 $s^{-1}$, preferably of 100 to 3000 $s^{-1}$, the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 3 to 15% w/w of rBLG and having a pH between 3 and 8, preferably between 4 and 6, b) Heating the aqueous solution of rBLG at a temperature comprised between 75 and 99° C., preferably between 8° and 90° C., for 5 to 30 minutes, and c) Applying simultaneously to the aqueous solution of rBLG a high shear rate treatment of 70 to 3000 $s^{-1}$, preferably of 100 to 3000 $s^{-1}$, and d) Cooling the microparticulated rBLG aqueous solution, preferably at a temperature lower than or equal to 70° C., the percentage being expressed in weight in relation to the total weight of the aqueous solution.

According to another preferred embodiment, the method for the preparation of microparticulated rBLG comprises the steps of:

a) Providing an aqueous solution of rBLG, said aqueous solution comprising from 5 to 15% w/w of rBLG and having a pH between 4 and 6, b) Heating the aqueous solution of rBLG at a temperature comprised between 75 and 99° C., preferably between 8° and 90° C., for 5 to 30 minutes, c) Applying simultaneously to the aqueous solution of rBLG a high shear rate treatment of 70 to 3000 $s^{-1}$, preferably of 100 to 3000 $s^{-1}$, and d) Cooling the microparticulated rBLG aqueous solution at a temperature comprised between 1 and 20° C., the percentage being expressed in weight in relation to the total weight of the aqueous solution.

It is understood that these embodiments are not limiting, and can further comprises one or mod additional steps as defined in the present invention.

Microparticulated Recombinant β-Lactoglobulin (rBLG)

The method of the invention as defined affords functionalized microparticulated rBLG. Then, another object of the invention is the microparticulated rBLG obtained according to the invention.

In order to have the desired properties, i.e stability to heat and suitable organoleptic properties, the particles size of microparticulated rBLG has to be of the order of micrometer (μm). It has been found that when the size of the particles size is too high, particles are unstable and does not provide satisfying organoleptic properties to the product. Alternatively, a low particle size does not provide stability to the particles and does convey watery sensory attributes to the product when creaminess is sought. It is understood that the expression "particle size" refers to the diameter of the particle.

Diameter of particles can more precisely be defined by the d90.3, d50.3 and d10.3 granulometric values. The values d90.3 means that 90% of the particles have a diameter less than said value. Similarly, the value d50.3 means that 50% of the particles have a diameter less than said value, and the value d10.3 means that 10% of the particles have a diameter less than said value. In some preferred embodiments, the d90.3, d50.3 and d10.3 size is measured by laser diffraction.

According to the invention, the particle size of microparticulated rBLG or the diameter of microparticulated rBLG refers to the granulometric value d50.3. It is understood that the defined particle size refers to an average particle size.

The microparticulated rBLG has preferably a size lower than 100 μm, more preferably lower than 50, and even more preferably lower than 25 μm.

Advantageously, the size of microparticulated rBLG particles is higher than 0.001 μm, preferably higher than 0.01 μm, more preferably higher than 0.05 μm and even more preferably higher or equal to 0.1 μm.

Preferably, the size of the particles of microparticulated rBLG is comprised between 0.1 and 20 μm, preferably between 0.1 and 18 μm, more preferably between 0.1 and 15 μm. In preferred embodiments, the microparticulated rBLG has a size comprised between 0.2 and 15 μm, preferably between 0.3 and 14 μm, more preferably between 0.4 and 13 μm, even more preferably between 0.4 and 12 μm, and still better between 0.4 and 11 μm. Advantageously, the size of microparticulated rBLG is comprised between 0.5 and 10 μm, and preferably between 1 and 10 μm, or even preferably between 1 and 6 μm.

In some preferred embodiments, the particle size of microparticulated rBLG is both defined by the d90.3 and d50.3 values. According to these embodiments, the microparticulated rBLG has preferably a d90.3 value comprised between 0.1 and 20 μm, preferably between 0.1 and 15 μm and a d50.3 value comprised between 1 and 10 μm. In other preferred embodiments, the microparticulated rBLG has a d90.3 value comprised between 0.1 and 15 μm and a d50.3 value comprised between 1 and 10 μm, preferably between 1 and 6 μm. Still in other preferred embodiments, the microparticulated rBLG has a d90.3 value comprised between 0.1 and 12 μm and a d50.3 value comprised between 1 and 10 μm, preferably between 1 and 6 μm.

Aqueous Solution of Microparticulated Recombinant β-Lactoglobulin (rBLG)

Another object of the present invention is an aqueous solution comprising microparticulated rBLG and one or more polysaccharides. In a particular embodiment, the aqueous solution of microparticulated rBLG comprises from 3 to 20% w/w of microparticulated rBLG, from 0.1 to 5% w/w of polysaccharide and water.

The aqueous solution of microparticulated rBLG according to the invention has a similar composition to the one of the rBLG aqueous solution as defined above. Consequently, the microparticulated rBLG content and the polysaccharide content are approximatively the same as for the rBLG aqueous solution. It is understood that, due to the treatments applied to the rBLG aqueous solution, the percentages defining the content of microparticulated rBLG and polysaccharides are modified according to the concentration of the microparticulated rBLG aqueous solution.

However, the ratios between the different components in the microparticulated rBLG aqueous solution are not altered, and thus are the same as for the rBLG aqueous solution.

In one embodiment, the polysaccharide/microparticulated rBLG ratio is lower or equal to 1/2, and preferably equal or lower than 1/3.

In another embodiment, the aqueous solution comprising microparticulated rBLG and polysaccharides has a polysaccharide/microparticulated rBLG ratio preferably ranging from 1/30 to 1/2, more preferably from 1/25 to 1/2, even more preferably from 1/20 to 1/2. In preferred embodiments, the polysaccharide/microparticulated rBLG ratio ranges from 1/20 to 1/3, preferably from 1/15 to 1/3, more preferably from 1/10 to 1/3

Advantageously, the microparticulated rBLG aqueous solution comprises microparticulated rBLG and polysaccharide with a polysaccharide/microparticulated rBLG ratio of around 1/6, around 1/5 or around 1/4.

Dry Microparticulated Recombinant β-Lactoglobulin (rBLG)

The present invention also relates to dry microparticulated rBLG obtained according to the method as defined above. Particularly, the invention relates to a dry composition comprising microparticulated rBLG and at least one polysaccharide. The composition of the invention preferably comprises from 45 to 95% w/w of microparticulated rBLG, the percentage being expressed in relation to the total weight of the dry composition.

In one embodiment, the dry composition of microparticulated rBLG comprises more than 45% w/w, more than 50% w/w, more than 55% w/w, more than 60% w/w, more than 65% w/w, or even more than 70% w/w of microparticulated rBLG, the percentage being expressed in relation to the total weight of the dry composition.

In another embodiment, the dry composition comprising microparticulated rBLG comprises less than 95% w/w, preferably less than 92% w/w, and more preferably less than 90% w/w of microparticulated rBLG, the percentage being expressed in relation to the total weight of the dry composition.

In some embodiments, the dry composition of microparticulated rBLG comprises between 48 and 95% w/w of microparticulated rBLG, preferably between 50 and 95% w/w, more preferably between 55 and 95% w/w, and even more preferably between 60 and 95% w/w. More preferably, the dry composition comprises between 60 and 92% w/w, preferably between 65 and 92% w/w, more preferably between 70 and 92% w/w, and even more preferably between 75 and 92% w/w of microparticulated rBLG, the percentage being expressed in weight in relation to the total weight of the dry composition. Advantageously, the dry microparticulated rBLG composition comprises a microparticulated rBLG content of 75 to 92% w/w, preferably of 80 to 92% w/w, and more preferably of 85 to 92% w/w, the percentage being expressed in weight in relation to the total weight of the dry composition.

The dry microparticulated rBLG composition can further comprise polysaccharides as defined above. Preferably, the dry microparticulated rBLG composition comprises at least one polysaccharide, said polysaccharide being preferably of fungal origin, and in particular isolated from filamentous fungi selected from the group of species of *Aspergillus* and *Trichoderma.*

When present, the polysaccharide content in the dry microparticulated rBLG composition ranges from 0 to 50% w/w in relation to the total weight of the dry composition.

When present, the polysaccharide content in the dry microparticulated rBLG composition is lower than 40% w/w, and preferably lower than 30% w/w, and more preferably lower than 20% w/w, the percentage being expressed in weight in relation to the total weight of the dry composition.

When present, the dry microparticulated rBLG composition comprises between 0 and 30% w/w of polysaccharides, preferably between 0 and 20% w/w, more preferably between 0 and 15% w/w, and more preferably between 0 and 10% w/w, the percentage being expressed in weight in relation to the total weight of the dry composition. Advantageously, the polysaccharide content in the dry composition of microparticulated rBLG is comprised between 0.01 and 8% w/w, preferably between 0.05 and 6% w/w, and more preferably between 0.1 and 5% w/w, the percentage being expressed in weight in relation to the total weight of the dry composition.

In an alternative way, when present, the content of polysaccharide in the dry microparticulated rBLG composition can be defined as a polysaccharide/microparticulated rBLG ratio. In this embodiment, the polysaccharide/microparticulated rBLG ratio in the dry composition is lower than or equal to 1/2, and preferably lower than or equal to 1/3.

Preferably, the dry composition comprising microparticulated rBLG and polysaccharides has a polysaccharide/microparticulated rBLG ratio ranging from 1/30 to 1/2, more preferably from 1/25 to 1/2, even more preferably from 1/20 to 1/2. In preferred embodiments, the polysaccharide/microparticulated rBLG ratio ranges from 1/20 to 1/3, preferably from 1/15 to 1/3, more preferably from 1/10 to 1/3.

Advantageously, the dry composition of microparticulated rBLG has a polysaccharide/microparticulated rBLG ratio of around 1/6, around 1/5 or around 1/4.

The particles of dry microparticulated rBLG in the dry composition have a size similar to the one the aqueous solution comprising microparticulated rBLG.

In one embodiment, the microparticulated rBLG particles size in the dry composition is lower than 100 μm, preferably lower than 50, and more preferably lower than 25 μm.

In another embodiment, the size of the particles of microparticulated rBLG is comprised between 0.1 and 20 μm, preferably between 0.1 and 18 μm, more preferably between 0.1 and 15 μm. Preferably, microparticulated rBLG has a size comprised between 0.2 and 15 μm, preferably between 0.3 and 14 μm, more preferably between 0.4 and 13 μm, even more preferably between 0.4 and 12 μm, and still better between 0.4 and 11 μm. Advantageously, the size of microparticulated rBLG is comprised between 0.5 and 10 μm, and preferably between 1 and 10 μm, or even preferably between 1 and 6 μm.

In some preferred embodiments, the particle size of microparticulated rBLG is both defined by the d90.3 and d50.3 values. According to these embodiments, the microparticulated rBLG has preferably a d90.3 value comprised between 0.1 and 20 μm, preferably between 0.1 and 15 μm and a d50.3 value comprised between 1 and 10 μm. In other preferred embodiments, the microparticulated rBLG has a d90.3 value comprised between 0.1 and 15 μm and a d50.3 value comprised between 1 and 10 μm, preferably between 1 and 6 μm. Still in other preferred embodiments, the microparticulated rBLG has a d90.3 value comprised between 0.1 and 12 μm and a d50.3 value comprised between 1 and 10 μm, preferably between 1 and 6 μm.

Advantageously, the composition comprising dry microparticulated rBLG comprises:

From 50 to 99% w/w of microparticulated rBLG,

From 0 to 30% w/w of polysaccharide, and

From 0 to 10% w/w of minerals, the percentage being expressed in weight in relation to the total weight of dry matter of the composition, and the size of the microparticulated rBLG being as defined above.

In another preferred embodiment, the composition comprising microparticulated rBLG comprises:

From 60 to 99% w/w of microparticulated rBLG,

From 0 to 25% w/w of polysaccharide, and

From 0 to 5% w/w of minerals, the percentage being expressed in weight in relation to the total weight of dry matter of the composition, and the size of the microparticulated rBLG being as defined above.

In another preferred embodiment, the composition comprising microparticulated rBLG comprises:

From 70 to 99% w/w of microparticulated rBLG,

From 5 to 20% w/w of polysaccharide, and

From 0 to 5% w/w of minerals, the percentage being expressed in weight in relation to the total weight of dry matter of the composition, and the size of the microparticulated rBLG being as defined above.

In another preferred embodiment, the composition comprising microparticulated rBLG comprises:

From 80 to 99% w/w of microparticulated rBLG,

From 5 to 20% w/w of polysaccharide, and

From 0 to 5% w/w of minerals, the percentage being expressed in weight in relation to the total weight of dry matter of the composition, and the size of the microparticulated rBLG being as defined above.

In another preferred embodiment, the composition comprising microparticulated rBLG comprises:

From 90 to 99% w/w of microparticulated rBLG,

From 5 to 15% w/w of polysaccharide, and

From 0 to 5% w/w of minerals, the percentage being expressed in weight in relation to the total weight of dry matter of the composition, and the size of the microparticulated rBLG being as defined above.

Use of Microparticulated Recombinant β-Lactoglobulin (rBLG)

The invention concerns the use of microparticulated rBLG according to the invention, either as a dry microparticulated rBLG composition or as a microparticulated rBLG aqueous solution as defined above, in particular for making food product comprising microparticulated rBLG, and in particular animal and non-animal dairy products.

In some preferred embodiments, following the dissolution of microparticulated rBLG, and/or the mixing of microparticulated rBLG with other food ingredients and water, the solution or the mix containing microparticulated rBLG can be processed into food products without the need of acidification. Such food products are for example pasteurized and sterilized milk, ice cream, cream dessert, processed cheese, hard cheese, etc.

Microparticulated rBLG according to the invention, in a dry form or as an aqueous solution are particularly suitable for the preparation of animal and non-animal dairy products, such as beverages, yoghurts, ice cream and cheese, or cereal bars.

Dairy Products Comprising Microparticulated rBLG

Dairy products comprising microparticulated rBLG according to the invention have advantageously the texture and sensation of "classic" dairy product, and in some embodiments, they are free from milk produced by an animal. These products may also be termed non-animal dairy analogues or non-animal dairy products (or dairy-like products).

In other embodiments, dairy products comprising microparticulated rBLG according to the invention, can comprise animal-derived component. These products are termed dairy products or animal dairy products.

Advantageously microparticulated rBLG has similar nutritional properties than animal BLG (i.e. complete proteins, limiting a.a score >100%).

Animal or non-animal dairy products may include one or more additional components chosen from proteins, texture agents, lipids, flavor compounds, sweetening agents, color balancing agents, ashes, vitamins, or any combinations thereof. Embodiments include animal or non-animal dairy products comprising animal derived components (i.e. animal dairy products), non-animal derived components (i.e. non-animal dairy products), or a combination thereof (animal dairy products).

The term "texture agent", as used herein, refers to any substance added to food products to modify their physical properties, particularly their texture and mouthfeel, without significantly affecting their flavor or nutritional value. Texture agents are widely used in the food industry to achieve desired textures, stabilize formulations, thicken liquids, and form gels in a variety of food products, contributing to the overall sensory experience of the food. It can be derived from numerous sources, such as for example plants, animals, and seaweeds.

Animal or non-animal dairy products of the present invention can also further include one or more texture agents. Examples of texture agents are Maltodextrin, native starches, modified starches, cellulose derivatives (e.g., microcrystalline cellulose), carrageenans, xanthan gum, guar gum, locust bean gum, acacia gum, agar-agar, gelatin, pectin, alginate, or plant proteins (e.g., soy proteins, pea proteins) and mixtures thereof.

The term "lipids" means one or more molecules (e.g., biomolecules) that include a fatty acyl group (e.g., saturated or unsaturated acyl chains). For example, the lipids include oils, phospholipids, free fatty acids, phospholipids, monoglycerides, diglycerides, and triglycerides and mixtures thereof. Non-limiting examples of lipids are described herein.

Lipids suitable in the animal or non-animal dairy products of the present invention can be selected from the group consisting of sunflower oil, coconut oil, tributyrin, mono- and di-glycerides, free fatty acids, phospholipids and mixtures thereof. In some embodiments of any of the compositions described herein, the free fatty acids are selected from the group of: butyric acid, caproic acid, caprylic acid, and capric acid and mixtures thereof. In some embodiments of any of the compositions described herein, the phospholipids are selected from soy lecithin phospholipids, sunflower lecithin phospholipids, cotton lecithin phospholipids, or rapeseed lecithin phospholipids and mixtures thereof. In some embodiments of any of the compositions described herein, the monoglycerides and diglycerides are plant-derived monoglycerides and diglycerides, or are bacteria-derived monoglycerides and diglycerides.

Lipids can also be plant-derived lipids, that is to say a lipid obtained from and/or produced by a plant (e.g. monocot or dicot).

The term "flavors", as used herein, refers to the taste and/or the aroma of a food or a drink. According to the invention, flavor compounds are preferably selected from the group consisting of: δ-decalactone, ethyl butyrate, 2-furyl methyl ketone, 2,3-pentanedione, γ-undecalactone, and δ-undecalactone and mixtures thereof.

"Sweetening agent" refers to a saccharide (e.g., a monosaccharide, a disaccharide, or a polysaccharide) or an artificial sweetener (e.g., a small molecule artificial sweetener or a protein artificial sweetener) that, when added to a composition, makes the composition taste sweet when ingested by a mammal, such as a human. Non-limiting examples of sweetening agents are described herein.

Examples of sweetening agents suitable for the animal or non-animal dairy products according to the invention are saccharides selected from the group consisting of: glucose, mannose, maltose, fructose, galactose, lactose, sucrose, monatin, and tagatose and mixtures thereof. In some embodiments sweetening agent is an artificial sweetener, and preferably selected from the group consisting of: stevia, aspartame, cyclamate, saccharin, sucralose, mogrosides, brazzein, curculin, erythritol, glycyrrhizin, inulin, isomalt, lacititol, mabinlin, malititol, mannitol, miraculin, monatin, monelin, osladin, pentadin, sorbitol, thaumatin, xylitol, acesulfame potassium, advantame, alitame, aspartame-acesulfame, sodium cyclamate, dulcin, glucin, neohesperidin dihydrochalcone, neotame, and P-4000, and mixtures thereof.

The term "color balancing agent" or "coloring agent" refers to an agent added to a composition to modulate the color of the composition, e.g., to make the color of the composition appear more similar to a mammal-produced milk. Non-limiting examples of color balancing agents or coloring agents include β-carotene and annatto. A color balancing agent or a coloring agent can be produced by or obtained from a plant.

The term "ash" is an art-known term and represents one or more ions, elements, minerals, and/or compounds that can be found in a mammal-produced milk. Non-limiting ions, elements, minerals, and compounds that are found in a mammal-produced milk, are for instance calcium, phosphorus, potassium, sodium, citrate, and chloride.

In some embodiments, animal or non-animal dairy products of the present invention may further comprise one or more ashes. The ash is preferably chosen from minerals. In some embodiments of these dairy products, the minerals are preferably chosen from sodium, potassium, calcium, magnesium, phosphorus, iron, copper, zinc, chloride, manganese, selenium, iodine, retinol, carotene, vitamins, vitamin D, vitamin E, vitamin B12, thiamin and riboflavin and mixtures thereof. In some embodiments of these animal or non-animal dairy products, the ash is preferably chosen among anions. In some embodiments of these animal or non-animal dairy products, the ashes are chosen among phosphate, citrate, sulfate, carbonate, and chloride and mixtures thereof.

The term "vitamin" refers to organic molecules (or a set of closely related molecules called vitamers) that are essential to an organism in small quantities for proper metabolic function. According to the invention, vitamins that can be used in the dairy products are preferably chosen from lipid soluble vitamins, water soluble vitamins, thiamin [vitamin B1], riboflavin [vitamin B2], niacin 0 [vitamin B3], pantothenic acid [vitamin B5], vitamin B6 [pyridoxine], vitamin B12 [cobalamin], vitamin C, folate, vitamins A, vitamin D, vitamin E, vitamin K and mixtures thereof.

In some embodiments, animal or non-animal dairy products according to the invention may further comprise fat. Fat includes triglycerides, and/or high-oleic oil. In some embodiments of these animal or non-animal dairy products, the high-oleic oil are chosen from mono unsaturates, oleic, linoleic, linolenic and saturates and mixtures thereof. In some embodiments of these animal or non-animal dairy products, the fats comprise short chain fatty acids. In some embodiments of these animal or non-animal dairy products, the short chain fatty acids are selected among butanoic, hexanoic, octanoic, and decanoic acids and mixtures thereof. In some embodiments of these animal or non-animal dairy products, one or more of the fats comprised trans-esterified fatty acids. In some embodiments of these animal or non-animal dairy products, one or more of the fats are isolated from plants. In some embodiments of these animal or non-animal dairy products, the plant is selected from one or more of the following: sunflower, corn, olive, soy, peanut, walnut, almond, sesame, cottonseed, canola, safflower, flax seed, palm, palm kernel, palm fruit, coconut, babassu, shea butter, mango butter, cocoa butter, wheat germ and rice bran oil.

In some embodiments, animal or non-animal dairy products can further comprise sugars, said sugars comprising galactose, sucrose, glucose, fructose and maltose and mixtures thereof. In some embodiments of these animal or non-animal dairy products, the dairy substitute food product is essentially free of lactose.

According to the invention, the animal or non-animal dairy products comprising microparticulated rBLG have preferably one or more characteristics of a classic dairy food product selected from the group consisting of: taste, aroma, appearance, handling, mouthfeel, density, structure, texture, elasticity, springiness, coagulation, binding, leavening, aeration, foaming, creaminess and emulsification.

Preferably, animal or non-animal dairy products according to the invention, i.e. comprising microparticulated rBLG, have improved or modified properties as compared to a classic dairy product. In some embodiments, the properties may be for example, but without limitation, the viscosity, the foaming effect, the buffering effect, storage time, opacity, smell, etc.

In some embodiments, the microparticulated rBLG can be processed into high protein food products. Such high protein food products are for example high protein yogurts, high protein UHT (ultra heat treatment) drinks, high protein fruit preparations, high protein cream cheeses, high protein snacks, high proteins bites, high proteins cereal bars, high protein ready to drink milk, high protein milk beverages, or high protein beverages.

In some embodiments, the non-animal dairy product is a vegan dairy product, and then can further comprise one or more of (a) a plant-derived oil; (b) a plant-derived starch: (c) a sugar; and (d) a salt. In some embodiments, the dairy product further comprises a flavoring selected from cheddar flavor, parmesan flavor or mozzarella flavoring.

In other embodiments, the animal or non-animal dairy products can comprise respectively one or more of animal-derived or non-animal derived beta lactoglobulin, serum albumin, lactoferrin, and transferrin. Preferably, in some embodiments of any of the compositions described herein, the beta-lactoglobulin is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth beta-lactoglobulin; the serum albumin is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth serum albumin; the lactoferrin is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth lactoferrin; and/or the transferrin is a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth transferrin protein.

In some embodiments, animal or non-animal dairy products comprising microparticulated rBLG according to the invention, further includes respectively one or more of: animal-derived or non-animal-derived kappa casein, beta casein, alpha S1 casein, and alpha S2 casein. The kappa/beta/alpha S1/alpha S2 casein can be a cow, human, sheep, goat, buffalo, camel, horse, donkey, lemur, panda, guinea pig, squirrel, bear, macaque, gorilla, chimpanzee, mountain goat, monkey, ape, cat, dog, wallaby, rat, mouse, elephant, opossum, rabbit, whale, baboons, gibbons, orangutan, mandrill, pig, wolf, fox, lion, tiger, echidna, or woolly mammoth kappa/beta/alpha S1/alpha S2 casein protein.

Suitable non-animal protein can be a native or recombinant non-animal protein, or hydrolyzed native or recombinant non-animal protein, or combinations thereof. Non-animal components can also derive from non-animal sources including naturally occurring or modified plants, algae, fungi, or microbes.

Examples of suitable plants include but are not limited to spermatophytes (spermatophyta), acrogymnospermae, angiosperms (magnoliophyta), ginkgoidae, pinidae, mesangiospermae, cycads, *Ginkgo*, conifers, gnetophytes, *Ginkgo biloba*, cypress, junipers, *Thuja*, cedarwood, pines, *Angelica*, caraway, coriander, cumin, fennel, parsley, dill, dandelion, helichrysum, marigold, mugwort, safflower, camomile, lettuce, wormwood, calendula, citronella, sages, thyme, chia seed, mustard, olive, coffee, *Capsicum*, eggplant, paprika, cranberry, kiwi, vegetable plants (e.g., carrot, celery), *Tagetes*, tansy, tarragon, sunflower, wintergreen, basil, hyssop, lavender, lemon *verbena*, marjoram, *Melissa*, patchouli, pennyroyal, peppermint, rosemary, sesame, spearmint, primroses, samara, pepper, pimento, potato, sweet potato, tomato, blueberry, nightshades, *Petunia*, morning glory, lilac, jasmin, honeysuckle, snapdragon, *Psyllium*, wormseed, buckwheat, amaranth, chard, *Quinoa*, spinach, rhubarb, jojoba, *Cypselea, Chlorella*, manila, hazelnut, canola, kale, bok choy, rutabaga, frankincense, myrrh, elemi, hemp, pumpkin, squash, curcurbit, manioc, *Dalbergia*, legume plants (e.g., alfalfa, lentils, beans, clovers, peas, fava coceira, frijole bola roja, frijole negro, *Lespedeza*, licorice, lupin, mesquite, carob, soybean, peanut, tamarind, *Wisteria, Cassia*, chickpea, garbanzo, fenugreek, green pea, yellow pea, snow pea, lima bean, fava bean), geranium, flax, pomegranate, cotton, okra, neem, fig, mulberry, clove, *Eucalyptus*, tea tree, niaouli, fruiting plants (e.g., apple, apricot, peach, plum, pear, nectarine), strawberry, blackberry, raspberry, cherry, prune, rose, tangerine, citrus (e.g., grapefruit, lemon, lime, orange, bitter orange, mandarin), mango, citrus bergamot, buchu, grape, broccoli, brussels, sprout, camelina, cauliflower, rape, rapeseed (canola), turnip, cabbage, cucumber, watermelon, honeydew melon, zucchini, birch, walnut, cassava, baobab, allspice, almond, breadfruit, sandalwood, macadamia, taro, tuberose, aloe vera, garlic, onion, shallot, vanilla, *Yucca*, vetiver, galangal, barley, corn, *Curcuma aromatica*, ginger, lemon grass, oat, palm, pineapple, rice, rye, sorghum, triticale, turmeric, yam, bamboo, barley, cajuput, *Canna*, cardamom, maize, oat, wheat, cinnamon, *Sassafras, Lindera benzoin*, bay laurel, avocado, ylang-ylang, mace, nutmeg, moringa, horsetail, oregano, cilantro, chervil, chive, aggregate fruits, grain plants, herbal plants, leafy vegetables, non-grain legume plants, nut plants, succulent plants, land plants, water plants, delbergia, millets, drupes, schizocarps, flowering plants, non-flowering plants, cultured plants, wild plants, trees, shrubs, flowers, grasses, herbaceous plants, brushes, lianas, cacti, green algae, tropical plants, subtropical plants, temperate plants, and derivatives and crosses thereof.

Examples of suitable algae include but are not limited to green algae (e.g., *Chlorella*), brown algae (e.g., *Alaria marginata, Analipus japonicus, Ascophyllum nodosum, Ecklonia* sp, *Eisenia bicyclis, Hizikia fusiforme, Kjellmaniella gyrata, Laminaria angustata, Laminaria longirruris, Laminaria Longissima, Laminaria ochotensis, Laminaria claustonia, Laminaria saccharina, Laminaria digitata, Laminaria japonica, Macrocystis pyrifera, Petalonia fascia, Scytosiphon lome*), red algae (e.g., Gigartinaceae, Soliericeae, *Chondrus crispus, Chondrus ocellatus, Eucheuma cottonii, Eucheuma spinosum, Furcellaria fastigiata, Gracilaria bursa-pastoris, Gracilaria lichenoides, Gloiopeltis furcata, Gigartina acicularis, Gigartina bursa-pastoris, Gigartina pistillata, Gigartina radula, Gigartina skottsbergii, Gigartina stellata, Palmaria palmata, Porphyra columbina, Porphyra crispata, Porhyra deutata, Porhyra perforata, Porhyra suborbiculata, Porphyra tenera, Porphyridium cruentum, Porphyridium purpureum, Porphyridium aerugineum, Rhodella maculate, Rhodella reticulata, Rhodella violacea*, Rhodophyceae, *Rhodymenia palmata*), and derivatives and crosses thereof.

Examples of suitable fungi include but are not limited to *Aspergillus* sp., *Aspergillus nidulans, Aspergillus niger, Aspergillus niger* var. *awamori, Aspergillus oryzae, Candida albicans, Candida etchellsii, Candida guilliermondii, Candida humilis, Candida lipolytica, Candida pseudotropicalis, Candida utilis, Candida versatilis, Chrysosporium lucknowense, Debaryomyces hansenii, Endothia parasitica, Eremothecium ashbyii, Fusarium* sp., *Fusarium gramineum, Fusarium moniliforme, Fusarium venenatum, Hansenula polymorpha, Kluyveromyces* sp., *Kluyveromyces lactis, Kluyveromyces marxianus, Kluyveromyces marxianus* var. *lactis, Kluyveromyces thermotolerans, Morteirella vinaceae* var. *raffinoseutilizer, Mucor miehei, Mucor miehei* var. Cooney et Emerson, *Mucor pusillus* Lindt *Myceliophthora thermophile, Neurospora crassa, Penicillium roquefortii, Physcomitrella patens, Pichia* sp., *Pichia pastoris, Pichia finlandica, Pichia trehalophila, Pichia koclamae, Pichia membranaefaciens, Pichia minuta* (*Ogataea minuta, Pichia lindneri*), *Pichia opuntiae, Pichia thermotolerans, Pichia salictaria, Pichia guercuum, Pichia pijperi, Pichia stiptis, Pichia methanolica, Rhizopus niveus, Rhodotorula* sp., *Saccharomyces* sp., *Saccharomyces bayanus, Saccharomyces beticus, Saccharomyces cerevisiae, Saccharomyces chevalieri, Saccharomyces diastaticus, Saccharomyces ellipsoideus, Saccharomyces exiguus, Saccharomyces florentinus, Saccharomyces fragilis, Saccharomyces pastorianus, Saccharomyces pombe, Saccharomyces sake, Saccharomyces uvarum, Sporidiobolus johnsonii, Sporidiobolus salmonicolor, Sporobolomyces roseus, Trichoderma, Trichoderma*

*reesei, Xanthophyllomyces dendrorhous, Yarrowia lipolytica, Zygosaccharomyces rouxii*, and derivatives and crosses thereof.

Examples of suitable microbes include but are not limited to firmicutes, cyanobacteria (blue-green algae), oscillatoriophcideae, bacillales, lactobacilloscillatoriales, bacillaceae, lactobacilloae, *Acetobacter suboxydans, Acetobacter xylinum, Actinoplane missouriensis, Arthrospira platensis, Arthrospira maxima, Bacillus cereus, Bacillus coagulans, Bacillus subtilus, Bacillus cerus, Bacillus licheniformis, Bacillus stearothermophilus, Bacillus subtilis, Escherichia coli, Lactobacillus acidophilus, Lactobacillus bulgaricus, Lactococcus lactis, Lactococcus lactis* Lancefield Group N, *Lactobacillus reuteri, Leuconostoc citrovorum, Leuconostoc dextranicum, Leuconostoc mesenteroides* strain NRRL B-512 (F), *Micrococcus lysodeikticus, Spirulina, Streptococcus cremoris, Streptococcus lactis, Streptococcus lactis* subspecies *diacetylactis, Streptococcus thermophilus, Streptomyces chattanoogensis, Streptomyces griseus, Streptomyces natalensis, Streptomyces olivaceus, Streptomyces olivochromogenes, Streptomyces rubiginosus, Tetrahymena thermophile, Tetrahymena hegewischi, Tetrahymena hyperangularis, Tetrahymena malaccensis, Tetrahymena pigmentosa, Tetrahymena pyriformis*, and *Tetrahymena vorax*, and *Xanthomonas campestris*, and derivatives and crosses thereof.

Animal or non-animal dairy products comprising microparticulated rBLG as defined in the present patent application preferably comprises from 0.5 to 25% w/w of microparticulated rBLG, the percentage being expressed in relation to the total weight of the composition. In preferred embodiments, animal or non-animal dairy products comprise from 5 to 15% w/w of microparticulated rBLG and at least another source of protein, preferably selected among whole milk, coco milk, and recombinant milk proteins such as beta-lactoglobuline, alpha-lactalbumine, alpha-S1 casein, alpha-S2 casein, kappa casein, beta casein, etc, the percentage being expressed in relation to the total weight of the composition. In one preferred embodiment, animal or non-animal dairy products comprise from 5 to 15% w/w of microparticulated rBLG, preferably from 6 to 10% w/w, and at least 85% of whole milk, the percentage being expressed in weight in relation to the total weight of the composition.

EXAMPLES

Figure 1:
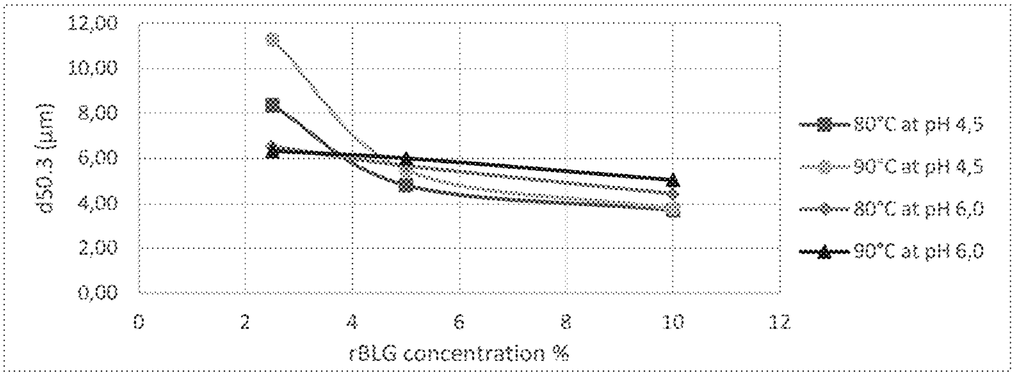
FIG. 1 represents the average diameter d50.3 of the particle size distribution of microparticulated rBLG produced in different conditions of rBLG concentrations, temperature and pH of the aqueous solution.

The present invention is further illustrated by the following examples.

Example 1: Production of Microparticulated rBLG at a Lab Scale rBLG used in the example 1 was produced by precision fermentation and has the composition as defined in table 1.

TABLE 1 rBLG composition in example 1. Total carbohydrates correspond to polysaccharides.

| Composition | Content | Unit |
|---|---|---|
| Total proteins (N % × 6.25) | 76.2 | g/100 g powder |
| Beta lactoglobulin | 75 | g/100 g powder |
| Total fat | 0.6 | g/100 g powder |
| Total carbohydrates | 19.2 | g/100 g powder |
| Moisture | 3.0 | g/100 g powder |
| Ash | 1.6 | g/100 g powder |
| Cu | 2.38 (+0.71) | mg/100 g powder |
| Ca | 413.0 (+123.9) | mg/100 g powder |
| Fe | 4.04 (+1.21) | mg/100 g powder |
| Mg | 110.0 (+33.0) | mg/100 g powder |
| P | 30.8 (+9.2) | mg/100 g powder |
| K | 54.3 (+16.3) | mg/100 g powder |

General Procedure

Solutions of rBLG were prepared by rehydrating rBLG powder in demineralized water. pH of the solutions was adjusted to pH 4 to 6 with HCl 1M. The solutions were covered to avoid evaporation of water, and heated at a temperature of 70, 80 and 90° C. for 20 minutes with simultaneous stirring at a shear rate of 500 $s^{-1}$. The solutions were finally cooled to 6° C. without stirring.

Simultaneous heat treatment and high shear was obtained using a rotational rheometer MCR 502 (Anton Paar Germany GmbH, Ostfildern, Germany) equipped with a coaxial cylinder geometry.

Tests

The solutions after simultaneous heat and shear treatments and cooling were subjected to various tests: particle size distribution, heat stability and acid stability.

Particle Size Distribution

The volume-weighted particle size distributions of protein solutions after heating, shearing and cooling were determined by static light scattering (Beckman Coulter LS 13 320 fitted with a Universal Liquid Module and control software v6.01, Beckman Coulter Inc., Miami, FL, USA). Between 100 and 300 μL of sample was added to the measurement chamber. An obscuration of between 3 and 7% with maximum Polarization Intensity Differential Scattering (PIDS) of 60% was adhered for all particle size measurements. All measurements were performed at room temperature (18-20° C.) and the preparations were run in threefold and in three measurement cycles for each measurement. A refractive index of 1.52 was used for BLG (designation: 152.rf780d PIDS included). The refractive index of the solvent (water) was 1.33. An imaginary refractive index of 0.00 was used for the particles and the solvent (LS 13 320 Particle Size Analyzer Manual. Instruction for Use LS 13 320 Laser Diffraction Particle Size Analyzer; Beckman Coulter: Brea, CA, USA, 2011).

Heat Stability Test

After simultaneous heat treatment and high shear rate treatment and cooling, protein solutions were poured in 2 ml tubes and placed in a 90° C. water batch during 10 min, then quickly cooled down using ice bath. Solutions were observed where absence or presence of a gel, a flocculate or a precipitate is noted.

In addition to visual observations, heat stability of the microparticulated protein solutions were also evidenced by comparing particle size distribution before and after the heat stability test (90° C., 10 min).

Acid Stability Test

GDL (Glucono-Delta Lactone) (0.75% w/w) was added to the solutions of protein after being submitted to simultaneous heat treatment and high shear rate treatment. The solutions were then left unstirred, in a steam room at 27° C., until pH 4.50 is reached, then stored at 5° C. during 24 h. After 24 hours, solution was observed to note if a gel was formed or not.

Results

Results are presented below in tables 2 and 3.

TABLE 2

Impact of heating temperature, pH and protein concentration under high shear conditions (500 $s^{-1}$), on particle size (μm). The d10.3, d50.3 and d90.3, represent the particle size distribution, i.e. the particle sizes at which 10, 50 and 90% of the particle volume is below or equal. The d3.2 is a mean diameter of the size distribution also called the sauter diameter.

| rBLG concentration (% w/w) | pH | Temperature (° C.) | d90.3 | d50.3 | d10.3 | d3.2 |
|---|---|---|---|---|---|---|
| 2.5 | 4.5 | 70 | 16.44 | 8.10 | 3.96 | 7.06 |
| 2.5 | 4.5 | 80 | 23.29 | 8.35 | 2.71 | 5.93 |
| 2.5 | 6 | 80 | 15.92 | 6.52 | 2.94 | 5.56 |
| 2.5 | 4.5 | 90 | 21.61 | 11.28 | 5.60 | 9.53 |
| 2.5 | 6 | 90 | 16.67 | 6.32 | 1.84 | 3.71 |
| 5 | 4.5 | 80 | 8.82 | 4.80 | 2.83 | 4.50 |
| 5 | 6 | 80 | 10.17 | 5.67 | 3.04 | 5.00 |
| 5 | 4.5 | 90 | 9.16 | 5.47 | 3.06 | 4.90 |
| 5 | 6 | 90 | 11.31 | 6.00 | 3.06 | 5.27 |
| 10 | 4.5 | 80 | 7.79 | 3.69 | 2.41 | 3.68 |
| 10 | 6 | 80 | 8.09 | 4.42 | 2.85 | 4.34 |
| 10 | 4.5 | 90 | 6.92 | 3.75 | 2.83 | 3.92 |
| 10 | 6 | 90 | 8.84 | 5.03 | 2.89 | 4.63 |

Particle sizes d50.3 between 11.28 and 3.69 μm were achieved and can be considered as a suitable range of microparticle sizes to improve creaminess in dairy applications. At a concentration of 2.5% larger particles were achieved at pH 4.5, while at higher concentrations (5%, 10%) slightly larger particles were obtained at pH 6.0 rather than 4.5. There was also observed a decrease in particle size with increasing concentration of protein (FIG. 1).

Samples comprising microparticulated rBLG and obtained according to the process described above, were submitted to heat stability test (as described above).

Figure 2:
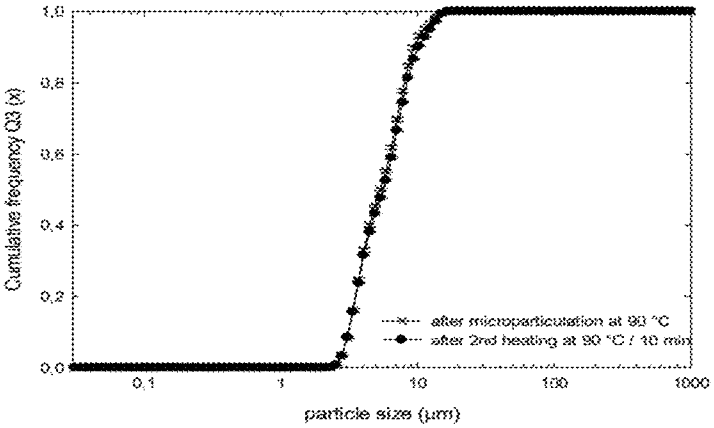
FIG. 2 represents the cumulative frequency of the particle size distribution (average of 3 replicates) of the microparticulated rBLG sample produced at 90° C., pH 6.0, 10% w/w protein and 500 $s^{-1}$ shear rate. A second curve has been obtained of the microparticulated sample after heat stability test (90° C./10 min).

Results are reported in table 3 (visual analysis) and in FIG. 2 (comparison of particle size distribution before and after heat stability test). Microparticulated rBLG samples produced at 90° C. (pH 4.5 or 6.0) from 2.5, 5.0 and 10% protein concentration under 500 $s^{-1}$ shear rate, which already gave suitable size of microparticules (table 2) are also stable: the samples are homogeneous, do not show phase separation, sedimentation or flocculation. As a confirmation, no significant differences between particles size distributions obtained before and after heat stability test (90° C./10 min) were reported on the samples that were visually considered as stable. The example of the microparticulated rBLG sample produced at 90° C., pH 6.0, 10% w/w protein and 500 $s^{-1}$ shear rate, is reported in FIG. 2. Particle size is unchanged after heat stability test, which further evidences heat stability in these conditions.

TABLE 3

Heat stability study performed on rBLG solutions microparticulated under high shear (500 $s^{-1}$) at 90° C. and pH 4.5 and 6.0.

| Conditions | Temperature | Protein concentration (%) | pH 4.5 | pH 6.0 |
|---|---|---|---|---|
| A | 90° C. | 2.5 | stable | stable |
| B | 90° C. | 5 | stable | stable |
| C | 90° C. | 10 | stable | stable |

Samples comprising microparticulated rBLG and obtained according to the process described above in conditions C described in Table 3 (90° C.; pH 6.0 under high shear (500 $s^{-1}$) from a 10% w/w initial rBLG solution, were submitted to acid stability test (as described above). The test resulted in no gel formation and no formation of visible particles/aggregates. The sample was liquid after the test which evidenced the stability of the microparticulated rBLG produced in conditions C against acidification to pH 4.5. On the contrary, microparticulated rBLG produced in conditions A were not stable and visible aggregates were observed. Thus, only the microparticulated rBLG obtained with the process of the present invention (condition C) are stable enough, even against acidification, which makes suitable for the production of animal and non-animal dairy products.

Example 2: Microparticulated rBLG Obtained Using a Scraped Surface Heat Exchanger (130 ml Batch, Around 10 g Protein/Batch)

General Procedure rBLG powder used here was produced by precision fermentation and has the composition as defined in table 1.

Solutions of 10% w/w of rBLG were prepared by rehydrating rBLG powder in demineralized water. pH of the solutions was adjusted to pH 6 with HCl 1M.

Microparticulation treatment with laboratory scale Scraped Surface Heat Exchanger (SSHE) (technical workshop of the university of Hohenheim, Stuttgart, Germany) was performed as described by (Filla et al., 2021; Protte et al., 2017): 130 mL of unheated rBLG solution was poured into the device. First, shear treatment was started by increasing stirrer to 200 rpm (corresponding to a representative shear rate of 65 $s^{-1}$) or 1000 rpm (corresponding to a representative shear rate of 327 $s^{-1}$), followed by initiation of the heat treatment. Solutions were heated via a water bath at 95° C. (temperature of the solution was 90° C.) connected to the double jacket of the SSHE for 20 min. After the heat treatment, the water supply was switched to cooling water (10° C.) for 10 min. Samples were stored cooled at 6° C.

Tests

The solutions after simultaneous heat and shear treatment and cooling were subjected to various tests: particle size distribution, heat stability and acid stability as described in example 1.

Results

Particle size of microparticulated rBLG were measured according to the methology described in Example 1. Results are presented in table 4 below.

TABLE 4

Particle size of microparticulated rBLG produced under high shear treatment (200 or 1000 rpm, correponding respectively to 65 $s^{-1}$ and 327 $s^{-1}$) at 90° C., pH 6 from 5 and 10% w/w rBLG aqueous solution.

| Condition | rBLG concetration (%) | High shear (rpm) | d50.3 (μm) |
|---|---|---|---|
| K | 5 (invention) | 1000 | 3.15 |
| L | 10 (comparative) | 200 | 26.65 |
| M | 10 (invention) | 1000 | 2.63 |

Treatment of rBLG aqueous solution (5 and 10% w/w) at 90° C. and pH 6.0 under high shear at 327 $s^{-1}$ (i.e. 1000 rpm) delivered microparticulated rBLG with a suitable size of d50.3 lower than 15 μm (Table 10). At a lower shear rate (65 $s^{-1}$), particle size was much bigger, with a diameter d50.3 of 26.65 μm.

Heat stability of microparticulated rBLG was also evaluated according to the methodology of example 1.

Microparticuated rBLG solutions obtained under conditions presented in Table 4 (conditions L and M) were submitted to heat stability test. Particle size before and after the test was measured using methodology of example 1.

Results are summarized in table 5.

TABLE 5

Particle size of microparticulated rBLG (d50.3 in μm) subjected to heat stability test or freeze-drying.

| Conditions | High shear (rpm) | d50.3 after micro-particulation (μm) | d50.3 after heat stability test (μm) | d50.3 after freeze-drying (μm) |
|---|---|---|---|---|
| L | 200 (comparative) | 26.65 | 26.2 | |
| M | 1000 (invention) | 2.63 | 2.6 | 2.71 |

Heat stability test showed that there was no change of the particle size before and after the heat stability test (90° C. for 10 min), demonstrating heat stability of microparticuled rBLG (table 5).

In addition to the heat stability, stability of microparticulated rBLG to freeze drying was evaluated. Microparticulated rBLG solutions (condition M, table 4) were freezed at −40° C. in small metal dishes. Frozen samples in dishes were placed in freeze dryer with −40° C. for 3 days. Powder was filled separately in a bag and vacuum packaged. Particle size of freeze dried microparticulated rBLG was measured and compared to particle size before freeze drying. No alteration of the particle size was observed after freeze drying (table 5), which demonstrates stability of microparticulated rBLG to freeze-drying.

Example 3: Morphology and Size of Microparticulated rBLG

A 2% w/w aqueous solution of microparticulated rBLG was prepared by rehydrating at room temperature in demineralized water microparticulated rBLG powder obtained with the methodology presented in Example 2 using conditions M (i.e. initial rBLG concentration was 10% w/w, shear rate was 327 $s^{-1}$ using laboratory scale SSHE, pH 6.0 and temperature at 90° C.) followed by freeze-drying. This solution was analyzed by scanning electron microscopy (SEM).

5 μl of 2% w/w microparticulated rBLG solution was deposited on a sillicon wafer. The drop was spread using a cone to ensure good distribution and it was let to dry. Afterwards the sample was covered with copper metallization. Images were collected by using a SEM FEI quanta 250 FEG (Fiel Emission Gun) equipment.

Figure 3:
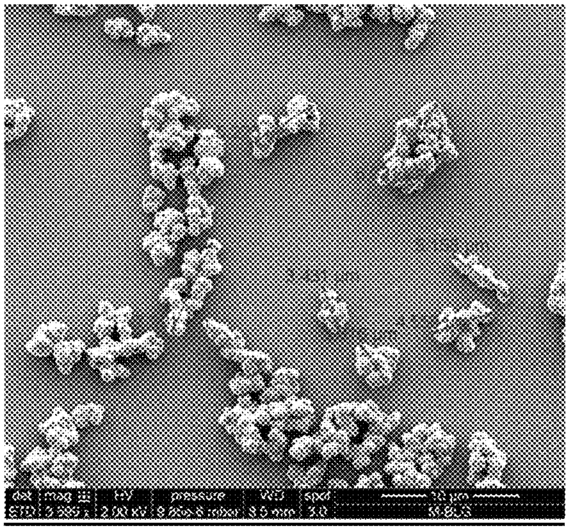
FIG. 3 is a scanning electron microscope (SEM) picture of microparticulated rBLG.

Pictures of microparticulated rBLG are presented in FIG. 3. The sample is composed of spherical aggregates ranging from 1 to 10 μm (FIG. 3).

Example 4: High Protein Yogurts Comprising Microparticulated rBLG

Yogurts have been prepared from microparticulated rBLG and/or rBLG in presence or absence of other protein sources (basic formula or hybrid formula) or with starch (potato starch ETENIA™ 457) and properties of yogurts have been analyzed.

General Procedure rBLG used in the Example 4 was produced by precision fermentation and has the composition as defined in table 6.

TABLE 6 rBLG composition in example 6. Total carbohydrates correspond to polysaccharides.

| Composition | Content | Unit |
|---|---|---|
| Total proteins (N × 6.25) | 79.7 | g/100 g powder |
| Beta lactoglobulin | 79.7 | g/100 g powder |
| Total fat | 0.6 | g/100 g powder |
| Total carbohydrates | 13.9 | g/100 g powder |
| Moisture | 3.0 | g/100 g powder |
| Ash | 3.5 | g/100 g powder |
| Cu | 1.82 (+0.55) | mg/100 g powder |
| Ca | 144.0 (+43.2) | mg/100 g powder |
| Fe | 3.25 (+0.98) | mg/100 g powder |
| Mg | 78.5 (+23.6) | mg/100 g powder |
| P | 266.0 (+79.8) | mg/100 g powder |
| K | 1180.0 (+354) | mg/100 g powder |

Microparticulated rBLG used in the example 4 has been obtained using the procedure described in example 2 with conditions M (i.e. initial rBLG concentration was 10% w/w, shear rate was 327 $s^{-1}$ using laboratory scale SSHE, pH 6.0 and temperature at 90° C.) followed by freeze-drying.

Model yoghurts of example 4 were produced using the following ingredients: Demineralized water; Organic coconut milk (KARA); Glucono-Delta-lactone (GDL); Pasteurized Whole Milk; Potato starch (ETENIA 457, Avebe).

The model yoghurts were produced using the following procedure: mixing ingredients with demineralized water under moderate agitation at room temperature in a beaker; pre-heating at 40° C. under moderate agitation for 10 min using a water bath; homogenizing the mix for 1 min at 13 500 rpm using an Ultraturrax; pasteurizing the mix at 85° C. for 10 min under moderate agitation using a water bath; cooling the mix to 27° C. by placing the beaker in a cooling cell; adding appropriate amount of GDL in powder form to the mix (between 1 and 2%) and leaving the mix unstirred at 27° C. during 3 hours in order to reach pH 4.5 in aseptic 40 ml polypropylene container; cooling the acidified mix at 4° C. in refrigerator overnight.

Yogurts compositions (before or after addition of GDL) are summarized in tables 7 and 8.

TABLE 7

Compositions of yogurts comprising rBLG and microparticulated rBLG (mBLG) in % w/w in relation to the total weight of the composition. H1 and S1 do not comprise rBLG or microparticulated rBLG.

| | Water | Whole milk | Coco milk | Potato starch | rBLG | mBLG |
|---|---|---|---|---|---|---|
| F1 3% rBLG (comparative) | 68.53 | — | 27.78 | — | 3.69 | — |
| F2 9% rBLG (comparative) | 61.15 | — | 27.78 | — | 11.07 | — |
| F3 3% rBLG 6% mBLG (invention) | 60.08 | — | 27.78 | — | 3.69 | 8.45 |
| H1 (control) | — | 100 | — | — | — | — |
| H2 6% rBLG (comparative) | — | 92.62 | — | — | 7.38 | — |
| H3 6% mBLG (invention) | — | 91.55 | — | — | — | 8.45 |
| S1 (control) | 67.8 | — | 27.8 | 4.4 | — | — |
| S2 9% rBLG (comparative) | 56.8 | — | 27.8 | 4.4 | 11.07 | — |
| S3 9% mBLG (invention) | 55.1 | — | 27.0 | 4.4 | — | 12.67 |

TABLE 8

Proximate composition of yoghurts (in g/100 g product) of example 4 comprising rBLG and microparticulated rBLG (mBLG).

| g/100 g | Total solids | Total Protein | Proteins from rBLG | Proteins from mBLG | Proteins from Milk | Lipids | Total Carbohydrates |
|---|---|---|---|---|---|---|---|
| F1 3% rBLG (comparative) | 9.1 | 3.5 | 3 | — | — | 4.4 | 0.5 |
| F2 9% rBLG (comparative) | 16.3 | 9.5 | 9.0 | — | — | 4.4 | 1.5 |
| F3 3% rBLG 6% mBLG (invention) | 17.3 | 9.5 | 3.0 | 6.0 | — | 4.4 | 2.1 |
| H1 (control) | 12.0 | 3.3 | — | — | 3.3 | 3.3 | 3.5 |
| H2 6% rBLG (comparative) | 18.3 | 9.1 | 6.0 | — | 3.1 | 3.1 | 4.3 |
| H3 6% mBLG (invention) | 19.2 | 9.0 | — | 6.0 | 3.0 | 3.0 | 4.8 |
| S1 (control) | 9.6 | 0.5 | — | — | — | 4.4 | 4.0 |
| S2 9% rBLG (comparative) | 20.1 | 9.5 | 9.0 | — | — | 4.4 | 5.4 |
| S3 9% mBLG (invention) | 21.7 | 9.5 | — | 9.0 | — | 4.4 | 6.3 |

Tests

Texture Analysis 20 mL yoghurts are produced in aseptic 40 ml polypropylene container for textural analysis using the method outlined below. A TA.XTPlus Texture Analyzer with a 5 kg load cell (Stable Micro System, Surrey UK) was used to characterize the physical properties of the yoghurts.

Samples were held in refrigerator at 4° C. overnight after production. Prior to testing they were equilibrated for 2 h to room temperature. A cylindrical probe (P/10 10 mm diameter) was used to perform texturometry tests at room temperature (20° C.) (One-Cycle Compression Test). The initial parameters were: pre-test speed, 1.00 mm/s; test speed, 5.00 mm/s; post-test speed, 5.00 mm/s; compression distance, 10.00 mm; trigger force, 5.00 g. The results included hardness (in g, defined as the maximum peak force during the compression), and consistency (or work of penetration in g·sec, defined as the area under the peak corresponding to the compression) are reported in table 9. The tests were carried out in duplicate.

Rheology

Viscosity of the yoghurts was determined at 10° C. using a Anton Paar MCR95 rheometer equipped with plan-plan geometry (parallel plate fixture with a gap of 1 mm between the fixture (PP25, 25 mm diameter) and sample plate was used) over a range of shear rates (from 0.01 to 100 s−1). Viscosity readings were plotted versus shear rate and viscosity at 50 $s^{-1}$ shear rate was reported in table 9.

Texture (consistency and hardness), viscosity, coagulation after pasteurization, olfactive properties of yogurts were analyzed, and results are reported in table 9.

TABLE 9

Measured properties of yogurts obtained from compositions described in table 9. Pasteurization was performed at 85° C. for 10 min; Coagulation was determined with H1 as reference; Smell was compared to odour of H1, and was noted +when an unpleasant odour was observed and −when no odour was detected compared to H1; nd = not determined.

| Composition | Coagulation after pasteurization | Consistency (g. sec.$^{-1}$) | Hardness (g) | Viscosity (Pa · s) (at 50 s$^{-1}$ shear rate and 10° C.) | Smell |
|---|---|---|---|---|---|
| F1 | NO | 71 | 49.2 | 4.1 | + |
| F2 | YES | 304 | 242 | 298.3 | ++ |
| F3 | NO | 64 | 49.9 | 5.4 | + |
| H1 | NO | 19 | 11 | 0.62 | 0 |
| H2 | YES | 607 | 440 | 29.7 | + |
| H3 | NO | 26 | 14.9 | 1.8 | − |
| S1 | NO | 26 | 17 | 5.9 | nd |
| S2 | YES | 55 | 35 | 45.6 | nd |
| S3 | NO | 31 | 22.1 | 10.6 | nd |

As reported in table 9, among all yogurt mixes, the ones that contain rBLG above 6% (F2, H2 and S2) have shown thermal coagulation during pasteurization treatment. In contrast, mixes that contain a low content of rBLG (F1, 3% w/w), no added proteins (H1 and S1) and microparticulated rBLG even in high concentration (F3, H3, and S3) (up to 9% w/w) did not show coagulation during pasteurization. The protein enrichment of yogurt with rBLG (at least from 6% w/w enrichment) in order to reach high protein content (9% w/w total proteins in example 6) and hence produce high protein products led to premature thermal coagulation of the mix during pasteurization, as opposed to protein enrichment with microparticulated rBLG, which did not induce premature thermal coagulation of the mix during pasteurization even when added in high concentration (up to 9% w/w).

Results of texture of finish yogurts (hardness and consistency) presented in table 9 showed that the addition in the mix of microparticulated rBLG to reach high protein content (F3, H3, S3) either did not increase or increased slightly hardness and consistency vs. control with low or no protein content. For example, F3 with 6% w/w microparticulated rBLG on top of 3% w/w rBLG (total protein content at 9% w/w) showed a hardness of 49.9 g vs. F1 that contains only 3% rBLG which showed a hardness of 49.2 g. For example, H3 with 6% w/w microparticulated rBLG on top of ~3% w/w milk proteins showed a hardness of 14.9 g vs. H1 that contains only ~3% w/w milk proteins which showed a hardness of 11 g. For example, S3 with 9% w/w microparticulated rBLG in starch based formula showed a hardness of 22.1 g vs. H1 that contains only 3% rBLG which showed a hardness of 17 g. Similar results were obtained on consistency. Similar results were obtained on viscosity. In contrast, addition in the mix of rBLG to reach high protein content (F3, H3, S3) did increase drastically hardness, consistency and viscosity vs. control yogurts with low or no protein content or vs. high protein yogurts at the same total protein content (i.e 9% w/w) but obtained with the addition of microparticulated rBLG. For example, F2 with 6% w/w rBLG on top of 3% w/w rBLG (total protein content at 9% w/w) showed a viscosity of 298.3 Pa·s which is much higher than F1 (4.1 Pa·s) and F3 (5.4 Pa·s) that contains respectively only 3% rBLG (F1) and 6% of microparticulated rBLG on top of 3% rBLG (F3). For example, H2 with 6% w/w rBLG on top of ~3% w/w milk proteins (total protein content at 9% w/w) showed a viscosity of 29.7 Pa·s which is much higher than H1 (0.62 Pa·s) and H3 (1.8 Pa·s) that contains respectively only ~3% milk proteins (H1) and 6% of microparticulated rBLG on top of ~3% milk proteins (H3). For example, S2 with 9% w/w rBLG in starch based formula showed a viscosity of 45.6 Pa·s which is much higher than S1 (5.9 Pa·s) and S3 (10.6 Pa·s) that contains respectively no protein (S1) and 9% of microparticulated (S3). Similar results were obtained on hardness and consistency (table 9).

The protein enrichment of yogurt with rBLG (at least from 6% w/w enrichment) in order to reach high protein content (9% w/w total proteins in example 6) and hence produce high protein products led to inappropriate texture showing too high viscosity, hardness or consistency, as opposed to protein enrichment with microparticulated rBLG, which only induced slight changes in texture even when added in high concentration (up to 9% w/w).

Figure 4:
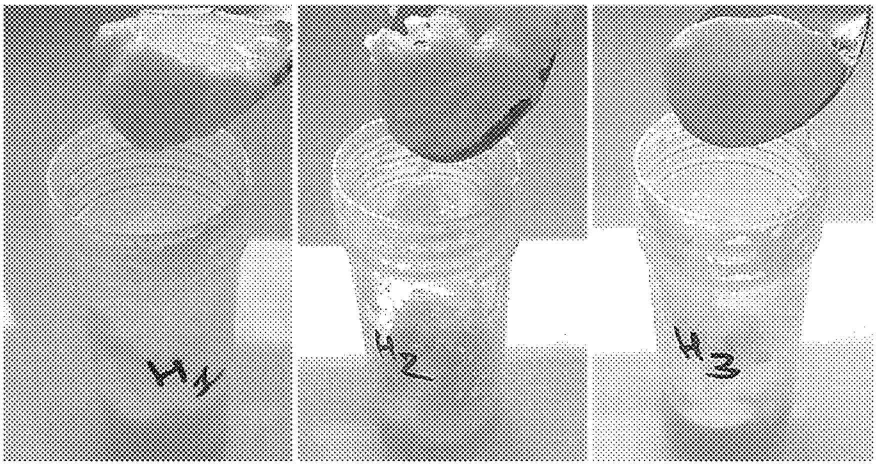
FIG. 4 is pictures showing yoghurts H1, H2, H3 and S1, S2, S3 that contain the ingredients reported in table 12 and that have the proximate composition reported in table 13
Figure 4:
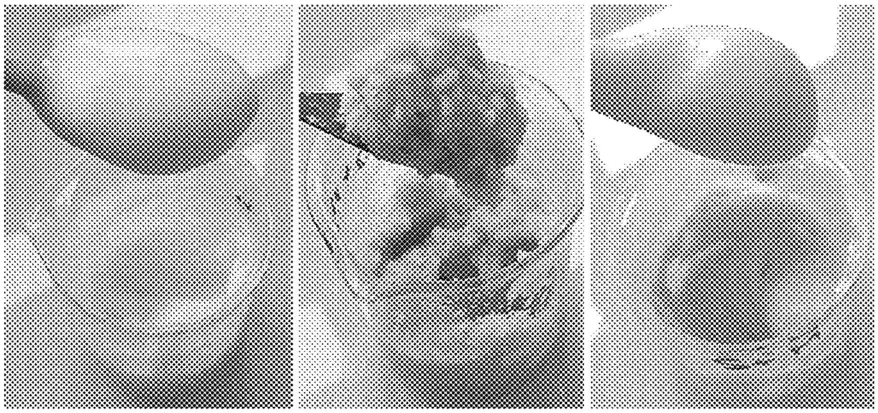

The previous results are confirmed by the yogurt pictures presented in FIG. 4 (yogurts H1, H2, H3 and S1, S2, S3). Both H1 containing only ~3% milk protein and H3 that contains 6% of microparticulated rBLG on top of ~3% milk proteins (total protein content at 9% w/w) showed typical yogurt aspect, H3 having a slightly more compact and smooth aspect than H1. In contrast, H2 yogurts that contains 6% w/w rBLG on top of ~3% w/w milk proteins (total protein content at 9% w/w) showed more heterogenous and more solid aspect, closer to heat-induced gel of whey proteins. Regarding the aspects of starch based yogurts (S1, S2 and S3), both S1 containing no protein and S3 that contains 9% of microparticulated rBLG showed very smooth, shiny and typical stirred yogurt aspect. In contrast, S2 yogurts that contains 9% w/w rBLG showed more heterogenous, closer to heat-coagulated whey protein gel.

Example 5: Foaming Properties of Microparticulated rBLG

General Procedure

A 10% w/w aqueous solution of microparticulated rBLG was prepared by rehydrating at room temperature in demineralized water microparticulated rBLG powder obtained with the methodology presented in Example 2 using conditions M (i.e. initial rBLG concentration was 10% w/w, shear rate was 327 s$^{-1}$ using laboratory scale SSHE, pH 6.0 and temperature at 90° C.) followed by freeze-drying.

Another 10% w/w aqueous solution of microparticulated whey protein was prepared by rehydrating at room temperature in demineralized water microparticulated whey protein powder (WPC 550, NZMP).

50 mL glass graduated cylinders were filled with 18 mL of solutions and then submitted to intense agitation with plunging Ultraturrax operated at 20 500 rpm for 1 min allowing air incorporation in the solutions. Difference in volume of solutions before and after agitation indicates the quantity of air incorporated in the solution and relates to the foaming capacity of the protein.

Results

TABLE 10

Volume (in mL) of microparticulated solutions of protein (microparticulated rBLG versus microparticulated whey protein) (10% w/w protein) before and after intense agitation treatment (Ultraturrax at 20500 rpm during 1 min).

| | Before stirring | After stirring |
|---|---|---|
| Microparticulated Whey proteins | 18 | 33 |
| Microparticulated rBLG | 18 | 21 |

Comparison of the volume a 10% w/w of microparticulated rBLG solution before and after stirring with Ultraturrax® at 20500 rpm shows a small increase. Before stirring the volume was 18 mL, whereas after stirring a volume of 21 mL was measured (Table 10). On the contrary, the same experiment carried out on 10% w/w microparticulated whey protein solution showed that the volume of the solution increased from 18 mL to 33 mL. The foaming effect of microparticulated rBLG is very low, making it suitable for the preparation of dairy products, as air incorporation in mixes can be detrimental to powder rehydration step and further steps of pumping, heat exchange or highpressure homogenization.

Example 6: Buffering Capacity of Microparticulated rBLG

General Procedure

A 9% w/w aqueous solution of microparticulated rBLG was prepared by rehydrating at room temperature in demineralized water microparticulated rBLG powder obtained with the methodology presented in Example 2 using conditions M (i.e. initial rBLG concentration was 10% w/w, shear rate was 327 $s^{-1}$ using laboratory scale SSHE, pH 6.0 and temperature at 90° C.) followed by freeze-drying.

Another 9% w/w aqueous solution of microparticulated whey protein was prepared by rehydrating at room temperature in demineralized water microparticulated whey protein powder (WPC 550, NZMP).

Figure 5:
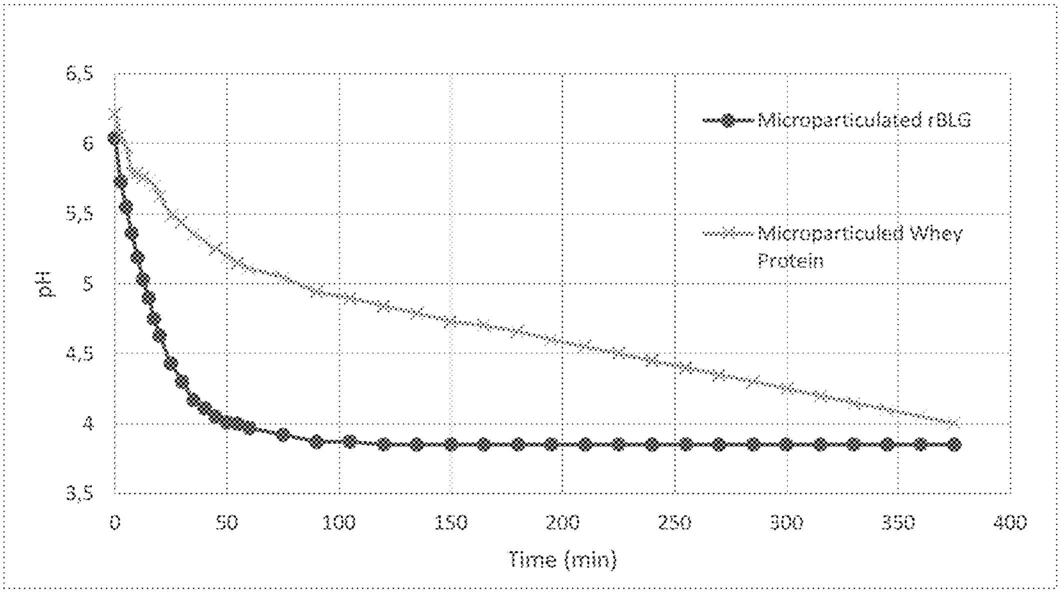
FIG. 5 represents the decrease of pH over time for solutions prepared from microparticulated rBLG at a concentration of 9% w/w and microparticulated whey protein at a concentration of 9% w/w after addition of 2% w/w glucono delta lactone (GDL).

Appropriate amount of glucono delta lactone (GDL) in powder form was added to reach 2% w/w GDL in the solutions. pH of the solutions was then monitored as a function of time during acidification (FIG. 5).

Results

FIG. 5 shows a difference in acidification rate between the two 9% w/w protein solutions. Acidification was much faster in the 9% w/w microparticulated rBLG than in the 9% w/w microparticulated whey protein solution, which means that the buffering effect of microparticulated rBLG solution is lower and results in a faster gelling by acidification. Then, a reduced process time is required for the acidification step, especially when high amount of protein need to be acidified, which is the case in the production of high protein yogurt without straining.

In addition, the lower buffering capacity of microparticulated rBLG will result in a lower quantity of acid (e.g. lactic acid) needed to be added or produced by lactic cultures to reach target pH (around 4.5) of finish products (for example, yogurts, fresh cheese etc.) which will result in improved organoleptic properties.

Example 7: High Protein UHT (Ultra High Temperature) Milks Comprising Microparticulated rBLG UHT milks were prepared from rBLG and microparticulated rBLG solutions.

General Procedure

Aqueous solutions of microparticulated rBLG at different protein concentrations (from 3% w/w to 9% w/w) were prepared by rehydrating at room temperature in demineralized water microparticulated rBLG powder obtained with the methodology presented in Example 2 using conditions M (i.e. initial rBLG concentration was 10% w/w, shear rate was 327 $s^{-1}$ using laboratory scale SSHE, pH 6.0 and temperature at 90° C.) followed by freeze-drying.

Aqueous solutions of rBLG in example 7 at different protein concentrations (from 3% w/w to 9% w/w) were prepared by rehydrating at room temperature in demineralized water rBLG powder obtained by precision fermentation and that has the composition as defined in table 11.

TABLE 11 rBLG composition in example 7. Total carbohydrates correspond to polysaccharides.

| Composition | Content | Unit |
|---|---|---|
| Total proteins (N × 6.25) | 81.2 | g/100 g powder |
| Beta lactoglobulin | 81.2 | g/100 g powder |
| Total fat | <0.5 | g/100 g powder |
| Total carbohydrates | 10.4 | g/100 g powder |
| Moisture | 5.3 | g/100 g powder |
| Ash | 1.6 | g/100 g powder |
| Cu | 1.59 | mg/100 g powder |
| Ca | 11.9 | mg/100 g powder |
| Fe | 3.8 | mg/100 g powder |
| Mg | 65.3 | mg/100 g powder |
| P | 88.9 | mg/100 g powder |
| K | 601 | mg/100 g powder |

Solutions were prepared in batches of 15 ml. pH was adjusted to 6.7 with 1 M NaOH. Approximately 5.5 mL was filled in stainless steel heating tubes. Experiments were performed in duplicates. Batch UHT heating with lab scale UHT (technical workshop of the University of Hohenheim, Stuttgart, Germany): heating tubes were placed in the pressure chamber (hanging vertically). Heating of the samples was rapidly realized by saturated steam condensation and lasted for 30 seconds. Cooling was realized within 30 seconds with ice-water. Heating temperature for these trials was 140° C. (steam 3 bar). Size particle was measured before and after heat treatment to assess the heat stability of the solutions and using the methodology presented in example 1.

Particle size was determined before and after UHT treatment of rBLG and microparticulated rBLG, and results are reported in tables 12 and 13. UHT treatment consists in heating the solution at 140° C. for 30 seconds with a heating ramp of 10 seconds and a cooling ramp of 30 seconds.

Results

TABLE 12

Particle size defined by d90.3, d50.3, d10.3 and Sauter diameter (d3.2) of solutions of rBLG before and after UHT treatment at pH 6.7 and 4.5 and as a function of protein concentration in solution.

| pH | UHT treatment | rBLG concentration (% w/w) | d90.3 (μm) | d50.3 (μm) | d10.3 (μm) | Sauter diameter (μm) |
|---|---|---|---|---|---|---|
| 6.7 | Before | 3 | 2.2 | 0.3 | 0.1 | 0.9 |
| | After | 3 | 2.5 | 0.4 | 0.2 | 1.1 |
| | After | 4 | 2.8 | 0.6 | 0.3 | 1.1 |
| | After | 5 | 3.8 | 1.0 | 0.4 | 2.6 |
| | After | 7 | 170.9 | 6.0 | 1.0 | 97.8 |
| | After | 9 | 222.9 | 53.3 | 4.1 | 108.4 |
| 4.5 | After | 3 | 493.1 | 200.1 | 18.5 | 190.0 |

TABLE 13

Particle size defined by d90.3, d50.3, d10.3 and Sauter diameter (d3.2) of solutions of microparticulated rBLG (mBLG) before and after UHT treatment at pH 6.7 and 4.5 and as a function of protein concentration in solution.

| pH | UHT treatment | mBLG Concentration (% w/w) | d90.3 (μm) | d50.3 (μm) | d10.3 (μm) | Sauter diameter (μm) |
|---|---|---|---|---|---|---|
| 6.7 | Before | 3 | 7.6 | 3.9 | 2.7 | 2.0 |
| | After | 3 | 5.1 | 3.1 | 2.2 | 1.6 |
| | After | 4 | 6.6 | 3.4 | 2.4 | 1.8 |
| | After | 5 | 6.5 | 3.3 | 2.4 | 1.7 |
| | After | 6 | 6.9 | 3.6 | 2.4 | 2.0 |
| | After | 7 | 6.9 | 3.7 | 2.3 | 2.1 |
| | After | 8 | 5.3 | 3.2 | 2.3 | 1.6 |
| | After | 9 | 5.9 | 3.3 | 2.3 | 1.6 |
| 4.5 | After | 3 | 5.4 | 3.3 | 2.3 | 1.7 |
| | After | 6 | 5.1 | 3.2 | 2.2 | 1.8 |
| | After | 9 | 5.1 | 3.2 | 2.2 | 1.5 |

At pH 6.7, rBLG is stable to UHT treatment when the concentration is equal or below 4% w/w (tables 12) as evidenced by the particle size that remained unchanged after UHT treatment. Above 5% w/w of rBLG, the solution coagulates (the Sauter diameter increases up to 108.4 μm). On the contrary, under the same conditions, microparticulated rBLG is stable to the UHT treatment for microparticulated rBLG solution comprising from 3 to 9% w/w protein as evidenced by the particle size that remains unchanged as compared to before UHT treatment (Table 13). Mixtures of rBLG (3% w/w) and microparticulated rBLG (3 to 6% w/w) are also stable when treated under the UHT conditions (results not shown).

Under acidic conditions (pH 4.5), a 3% w/w rBLG solution is not stable (Table 12) as shown by the Sauter dimeter of 190 μm. This is not the case of a 3% w/w microparticulated rBLG solution. Under the same conditions, the Sauter diameter remains constant around 1 or 2 μm for microparticulated rBLG solution of 3 to 9% w/w protein (Table 13) which evidenced UHT stability.

Example 8: Lipase Activity and Microparticulation Process

Lipase activity was screened in rBLG sample and microparticulated rBLG samples.

Recombinant BLG ingredients can contain enzymes produced by microbial hosts. Some of these enzymes are degrading lipids in food product applications which generate volatile compounds involved in detrimental off-notes. Enzymes with lipase activity can have similar size and molecular weight than BLG. Therefore, it is difficult to separate them by non-thermal physical process (frontal filtration, tangential filtration or centrifugation).

Procedure

Protein Samples rBLG sample was produced by precision fermentation and has the composition as defined in table 1 of example 1. Microparticulated rBLG was obtained from this rBLG sample with the methodology presented in Example 2 using conditions M (i.e. initial rBLG concentration was 10% w/w, shear rate was 327 $s^{-1}$ using laboratory scale SSHE, pH 6.0 and temperature at 90° C.) followed by freeze-drying.

Lipase Activity Assay

Lipase substrate specificity was determined using the pNP-assay (p-nitrophenyl palmitate) according to Stemler and Scherf (2022). Stock solutions (10 mmol/L) of pNP-derivatives were prepared in acetonitrile: 2-propanol (1:4, v:v) and stored frozen. The stock solutions were diluted with an assay buffer (50 mmol/L Tris-HCl, 1 mmol/L CaCl2, 0.3% Triton X-100, pH 7.5) directly before use. Lipases were dissolved at 1 mg/mL in the lipase buffer (50 mmol/L Tris-HCl, 1 mmol/L CaCl2, pH 7.5). For calibration, p-nitrophenol solutions from 0.05 mmol/L to 0.25 mmol/L were prepared using an assay buffer. The analysis was carried out in 96-well plates. Lipase solution (10 μL) was added to 190 μL of substrate working solution or 190 μL of assay buffer (lipase control) or 190 μL of calibration solutions (calibration). The absorbance at 410 nm was recorded at 30° C. for 60 min. The absorbance of the released p-nitrophenol was corrected by subtracting both lipase control and substrate control at the corresponding time. Lipase activity values of the samples were normalized to protein concentration of the sample solutions.

Results

Figure 6:
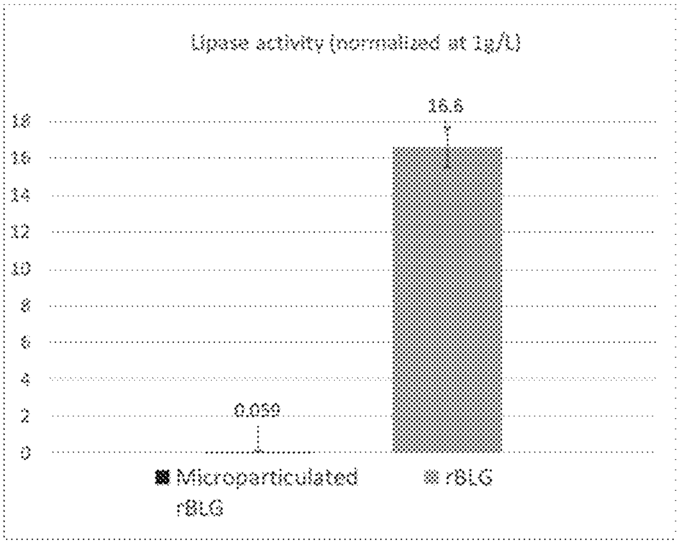
FIG. 6 represents the lipase activity in microparticulated rBLG and rBLG solutions.

Results of lipase activity for rBLG and Microparticulated rBLG are presented in FIG. 6. A sharp decrease in lipase activity was measured in microparticulated rBLG sample as compared to rBLG sample. This drastic reduction of lipase activity is also correlated with a decrease in unpleasant smell in coconut fat based yogurts formulated with microparticulated rBLG as compared to the ones formulated with rBLG (table 9).

It was then found that lipase was present in the rBLG samples. However, following microparticulation process according to the invention, lipase activity was decreased. The microparticulation process is thus responsible of the drastic reduction of lipase activity which improves the organoleptic properties of product applications, such as the one that contain lipids.

The invention claimed is:

1. A method for the preparation of microparticulated recombinant beta-lactoglobulin (rBLG) of non-animal origin comprising the steps of:

a) providing an aqueous solution of rBLG of non-animal origin, wherein said aqueous solution comprises from 3 to 20% w/w of rBLG by weight in relation to the total weight of the aqueous solution, and has a pH of from 3 to 8 or from 4 to 8, b) heating the aqueous solution of rBLG at a temperature of from 82 to 99° C., and c) applying a high shear rate treatment of at least 70 $s^{-1}$ to the aqueous solution of rBLG, to afford a microparticulated rBLG aqueous solution, wherein the microparticulated rBLG is in the form of aggregates having an average particle size of from 0.1 to 15 μm, and wherein particle size for said aggregates of microparticulated rBLG is heat stable as determined by a heat stability test at 90° C. for 10 min.

2. The method according to claim 1, wherein the rBLG concentration in the aqueous solution of step a is from 5 to 20% w/w or from 8 to 20% w/w by weight in relation to the total weight of the aqueous solution.

3. The method according to claim 1, wherein the pH of the aqueous solution of step a is from 4.5 to 7 or from 5.5 to 6.5.

4. The method according to claim 1, wherein the heating step in step b and the high shear rate treatment in step c are performed simultaneously.

5. The method according to claim 1, wherein the high shear rate treatment in step c is performed after the heating step in step b.

6. The method according to claim 1, wherein the method further comprises one or more steps selected among: a step d of cooling the aqueous solution to a temperature lower than 65° C., a step e of concentrating the aqueous solution, and a step f of drying the aqueous solution.

7. The method according to claim 1, wherein the aqueous solution of step a further comprises at least one polysaccharide.

8. The method according to claim 7, wherein the polysaccharide/rBLG ratio is from 1/3 to 1/30.

9. The method according to claim 1, wherein the rBLG of non-animal origin is obtained from a fungus.

10. A microparticulated rBLG of non-animal origin obtained from the process according to claim 1.

11. The microparticulated rBLG of non-animal origin according to claim 10, wherein the rBLG is in the form of aggregates, said aggregates having an average particle size of from 1 to 10 μm, or from 1 to 6 μm.

12. The method according to claim 9, wherein the fungus is of the genus *Aspergillus*.

13. An animal or non-animal dairy product comprising the microparticulated rBLG of non-animal origin according to claim 10.

* * * * *